(12) United States Patent
Lehoux et al.

(10) Patent No.: US 8,420,592 B2
(45) Date of Patent: Apr. 16, 2013

(54) METHODS OF TREATMENT USING SINGLE DOSES OF ORITAVANCIN

(75) Inventors: Dario Lehoux, Terrebonne (CA);
Thomas R. Parr, Indianapolis, IN (US);
Gregory Moeck, St. Laurent (CA);
Pierre Etienne, Montreal (CA)

(73) Assignee: The Medicines Company, Parsippany, NJ (US)

( * ) Notice: Subject to any disclaimer, the term of this patent is extended or adjusted under 35 U.S.C. 154(b) by 0 days.

(21) Appl. No.: 13/060,811

(22) PCT Filed: Aug. 29, 2009

(86) PCT No.: PCT/US2009/055466
§ 371 (c)(1),
(2), (4) Date: Apr. 12, 2011

(87) PCT Pub. No.: WO2010/025438
PCT Pub. Date: Mar. 4, 2010

(65) Prior Publication Data
US 2011/0201546 A1 Aug. 18, 2011

Related U.S. Application Data

(60) Provisional application No. 61/093,314, filed on Aug. 30, 2008, provisional application No. 61/093,497, filed on Sep. 2, 2008.

(51) Int. Cl.
*A01N 37/18* (2006.01)
*A61K 38/04* (2006.01)

(52) U.S. Cl.
USPC ............... 514/1.1; 514/2.6; 514/2.7; 514/3.1

(58) Field of Classification Search ........................ None
See application file for complete search history.

(56) References Cited

U.S. PATENT DOCUMENTS

2003/0176327 A1* 9/2003 Cassell et al. ............... 514/8
2004/0147441 A1 7/2004 Leach

FOREIGN PATENT DOCUMENTS

WO 99/10006 3/1999
WO 00/66144 11/2000
WO 2008/097364 8/2008

OTHER PUBLICATIONS

Boylan et al, Pharmacodynamics of Oritavancin (LY333328) in a Neutropenic-Mouse Thigh Model of *Staphylococcus aureus* Infection, Antimicrobial Agents and Chemotherapy, May 2003, p. 1700-1706.*
Fetterly et al, Pharmacokinetics of Oritavancin in Plasma and Skin Blister Fluid following Administration of a 200-Milligram Dose for 3 Days or a Single 800-Milligram Dose, Antimicrobial Agents and Chemotherapy, Jan. 2005, p. 148-152.*
Bhavnani, S.M. et al., Pharmacokinetics, safety, and tolerability of ascending single intravenous doses of oritavancin administered to healthy human subjects. Diagnostic Microbiology and Infectious Disease 50 (2004), 95-102.
Lee, S.Y. et al., Antimicrobial management of complicated skin and skin structure infections in the era of emerging resistance, Surgical Infections, 2005, vol. 6, No. 3, pp. 283-295.
Examination Report dated Oct. 15, 2012, from the New Zealand Intellectual Property Office in corresponding New Zealand Application No. 591525.
Printout from ClinicalTrials.gov website, entitled "A Study for Patients with Complicated Skin and Skin Structure Infections (SIMPLIFI)", ID No. NCT00514527, indicated as first received by NIH on Aug. 8, 2007.
Mercier, R.C. et al., Oritavancin: a new avenue for resistant Gram-positive bacteria, Expert Rev. Anti. Infect. Ther., 2005, vol. 3, No. 3, pp. 325-332.
Supplementary European Search Report dated Sep. 19, 2012, from the European Patent Office in corresponding European Application No. 09810708.9.

* cited by examiner

*Primary Examiner* — Cecilia J Tsang
*Assistant Examiner* — Sergio Coffa
(74) *Attorney, Agent, or Firm* — Roylance, Abrams, Berdo & Goodman LLP

(57) ABSTRACT

Glycopeptide antibiotics, such as oritavancin, demonstrate significant activity against a wide range of bacteria. Methods for the treatment, prophylaxis and prevention of bacterial infection and disease in animals, including humans, using a single dose of oritavancin over the course of therapy, are described.

4 Claims, 5 Drawing Sheets

All doses are included (subjects may have had more than 1 dose)

All doses are included (subjects may have had more than 1 dose)

METHODS OF TREATMENT USING SINGLE DOSES OF ORITAVANCIN

BACKGROUND OF THE INVENTION

Oritavancin diphosphate (oritavancin) is a semi-synthetic lipoglycopeptide derivative of a naturally occurring glycopeptide. Its structure confers potent antibacterial activity against gram-positive bacteria, including vancomycin-resistant enterococci (VRE), methicillin- and vancomycin-resistant staphylococci, and penicillin-resistant streptococci. The rapidity of its bactericidal activity against exponentially-growing *S. aureus* (≧3-log reduction within 15 minutes to 2 hours against MSSA, MRSA, and VRSA) is one of the features that distinguishes it from the prototypic glycopeptide vancomycin (McKay et al., *J Antimicrob Chemother.* 63(6): 1191-9 (2009), Epub 2009 Apr. 15).

Oritavancin inhibits the synthesis of peptidoglycan, the major structural component of the bacterial cell wall by a mechanism that is shared with glycopeptides, such as vancomycin (Allen et al., *Antimicrob Agents Chemother* 41(1):66-71 (1997); Cegelski et al., *J Mol Biol* 357:1253-1262 (2006); Arhin et al., Poster C1-1471: Mechanisms of action of oritavancin in *Staphylococcus aureus* [poster]. 47*th Intersci Conf Antimicro Agents Chemo*, Sep. 17-20, 2007; Chicago, Ill.). Oritavancin, like vancomycin, binds to the Acyl-D-Alanyl-D-Alanine terminus of the peptidoglycan precursor, lipid-bound N-acetyl-glucosamine-N-acetyl-muramic acid-pentapeptide (Reynolds, *Eur J Clin Microbiol Infect Dis* 8(11): 943-950 (1989); Nicas and Allen, Resistance and mechanism of action. In: Nagarajan R, editor. *Glycopeptide antibiotics*. New York: Marcel Dekker 195-215 (1994); Allen et al., *Antimicrob Agents Chemother* 40(10):2356-2362 (1996); Allen and Nicas, *FEMS Microbiology Reviews* 26:511-532 (2003); Kim et al., *Biochemistry* 45:5235-5250 (2006)). However, oritavancin inhibits cell wall biosynthesis even when the substrate is the altered peptidoglycan precursor that is present in VRE and vancomycin-resistant *S. aureus* (VRSA). Thus, the spectrum of oritavancin antibacterial activity extends beyond that of vancomycin to include glycopeptide-resistant enterococci and staphylococci (Ward et al., *Expert Opin Investig Drugs* 15:417-429 (2006); Scheinfeld, *J Drugs Dermatol* 6:97-103 (2007)). Oritavancin may inhibit resistant bacteria by interacting directly with bacterial proteins in the transglycosylation step of cell wall biosynthesis (Goldman and Gange, *Curr Med Chem* 7(8):801-820 (2000); Halliday et al., *Biochem Pharmacol* 71(7):957-967 (2006); Wang et al., Poster C1-1474: Probing the mechanism of inhibition of bacterial peptidoglycan glycotransferases by glycopeptide analogs. 47*th Intersci Conf Antimicro Agents Chemo*, Sep. 17-20, 2007). Oritavancin also collapses transmembrane potential in gram positive bacteria, leading to rapid killing (McKay et al., Poster C1-682: Oritavancin disrupts transmembrane potential and membrane integrity concomitantly with cell killing in *Staphylococcus aureus* and vancomycin-resistant Enterococci. 46*th Intersci Conf Antimicro Agents Chemo*, San Francisco, Calif., Sep. 27-30, 2006). These multiple effects contribute to the rapid bactericidal activity of oritavancin.

Oritavancin is in clinical development against serious gram-positive infections, where administration of the drug is via intravenous infusion using several dosages administered over a series of days. The development of alternative dosing regimens for the drug could expand treatment options available to physicians. The present invention is directed to novel dosing regimens.

BRIEF SUMMARY OF THE INVENTION

As disclosed herein, it has been discovered that the glycopeptide antibiotic oritavancin, also known as $N^{DSACC}$-(4-(4-chlorophenyl)benzyl)A82846B and LY333328, demonstrates clinically significant therapeutic activity against bacterial infections when administered to a subject in one dose over a course of therapy. The present invention is directed to methods of treatment, prophylaxis and/or prevention of bacterial infections in a subject, such as a human, using one dose of oritavancin (or its pharmaceutically acceptable salts, hydrates, or solvates thereof, or a mixture thereof).

In a first embodiment, the present invention is directed to methods of treating bacterial infections in a subject by administering one dose of oritavancin, or a pharmaceutically acceptable salt thereof, preferably formulated as a pharmaceutical composition, over a course of therapy to a subject.

In a first aspect of this embodiment, the present invention is directed to a method of treating a bacterial infection in a subject, comprising administering one dose of a therapeutically effective amount of a pharmaceutical composition comprising oritavancin, or a pharmaceutically acceptable salt thereof, and a pharmaceutically acceptable carrier or diluent, over a course of therapy to a subject having a bacterial infection, thereby treating a bacterial infection in a subject. In a preferred aspect, the pharmaceutical composition comprises at least about 400 mg oritavancin, or a pharmaceutically acceptable salt thereof. In a further preferred aspect, the pharmaceutical composition comprises between about 400 mg to about 1800 mg oritavancin, or a pharmaceutically acceptable salt thereof. In specific aspects, the pharmaceutical composition comprises about 800 mg, 900 mg, 1000 mg, 1100 mg, or 1200 mg oritavancin, or a pharmaceutically acceptable salt thereof.

In a variation of this first aspect, a single subsequent dose of oritavancin may be administered to the subject. Thus, the method of the first aspect may further comprise administering a second dose of a therapeutically effective amount of a pharmaceutical composition comprising oritavancin, or a pharmaceutically acceptable salt thereof, and a pharmaceutically acceptable carrier or diluent, within the course of therapy. Preferably, the second dose comprises an amount of oritavancin less than or equal to that of the first dose. Also preferably, the second dose is administered about 4 days or more after the first dose.

In a second aspect of this embodiment, the present invention is directed to a method of treating a bacterial infection in a subject, comprising administering one dose of a pharmaceutical composition comprising oritavancin, or a pharmaceutically acceptable salt thereof, and a pharmaceutically acceptable carrier or diluent, over a course of therapy to a subject having a bacterial infection, in an amount sufficient to achieve a maximum plasma concentration ($C_{max}$) of oritavancin of not less than about 20 μg/mL. In preferred aspects, the $C_{max}$ of oritavancin is not less than about 40 μg/mL, 60 μg/mL, or 80 μg/mL.

In a variation of this second aspect, a single subsequent dose of oritavancin may be administered to the subject. Thus, the method of the second aspect may further comprise administering a second dose of a therapeutically effective amount of a pharmaceutical composition comprising oritavancin, or a pharmaceutically acceptable salt thereof, and a pharmaceutically acceptable carrier or diluent, within the course of therapy. Preferably, the second dose comprises an amount of oritavancin less than or equal to that of the first dose. Also preferably, the second dose is administered about 4 days or more after the first dose.

In a third aspect of this embodiment, the present invention is directed to a method of treating a bacterial infection in a subject, comprising administering one dose of a pharmaceutical composition comprising oritavancin, or a pharmaceutically acceptable salt thereof, and a pharmaceutically acceptable carrier or diluent, over a course of therapy to a subject having a bacterial infection, in an amount sufficient to achieve an area under the concentration curve (AUC 0-24 hr) of oritavancin of at least about 20 μg*h/mL. In preferred aspects, the AUC 0-24 hr of oritavancin is at least about 40 μg*h/mL, 80 μg*h/mL, or 120 μg*h/mL.

In a variation of this third aspect, a single subsequent dose of oritavancin may be administered to the subject. Thus, the method of the third aspect may further comprise administering a second dose of a therapeutically effective amount of a pharmaceutical composition comprising oritavancin, or a pharmaceutically acceptable salt thereof, and a pharmaceutically acceptable carrier or diluent, within the course of therapy. Preferably, the second dose comprises an amount of oritavancin less than or equal to that of the first dose. Also preferably, the second dose is administered about 4 days or more after the first dose.

In a second embodiment, the present invention is directed to methods of providing prophylaxis for bacterial infections in a subject by administering one dose of oritavancin, or a pharmaceutically acceptable salt thereof, preferably formulated as a pharmaceutical composition, over a course of therapy to a subject.

In an aspect of this embodiment, the present invention is directed to a method of providing prophylaxis for a bacterial infection in a subject, comprising administering one dose of a therapeutically effective amount of a pharmaceutical composition comprising oritavancin, or a pharmaceutically acceptable salt thereof, and a pharmaceutically acceptable carrier or diluent, over a course of prophylaxis to a subject at risk of developing a bacterial infection, thereby providing prophylaxis for a bacterial infection in a subject. In a preferred aspect, the pharmaceutical composition comprises at least about 200 mg oritavancin, or a pharmaceutically acceptable salt thereof. In a further preferred aspect, the pharmaceutical composition comprises between about 200 mg to about 1800 mg oritavancin, or a pharmaceutically acceptable salt thereof. In specific aspects, the pharmaceutical composition comprises about 300 mg, 400 mg, 500 mg, 600 mg, 700 mg or 800 mg oritavancin, or a pharmaceutically acceptable salt thereof. In preferred aspects, prophylaxis is maintained for at least about 4, 8 or 12 hours. In an alternative aspect, prophylaxis is maintained is for the duration of a surgical procedure, a dental procedure or an invasive medical procedure.

In a variation of this aspect, a single subsequent dose of oritavancin may be administered to the subject. Thus, the method of this embodiment may further comprise administering a second dose of a therapeutically effective amount of a pharmaceutical composition comprising oritavancin, or a pharmaceutically acceptable salt thereof, and a pharmaceutically acceptable carrier or diluent, within the course of therapy. Preferably, the second dose comprises an amount of oritavancin less than or equal to that of the first dose.

In a third embodiment, the present invention is directed to methods of preventing bacterial infections in a subject by administering one dose of oritavancin, or a pharmaceutically acceptable salt thereof, preferably formulated as a pharmaceutical composition, over a course of therapy to a subject.

In an aspect of this embodiment, the present invention is directed to a method of preventing a bacterial infection in a subject, comprising administering one dose of a therapeutically effective amount of a pharmaceutical composition comprising oritavancin, or a pharmaceutically acceptable salt thereof, and a pharmaceutically acceptable carrier or diluent, over a course of prevention to a subject at risk of exposure to infectious bacteria, thereby preventing a bacterial infection in a subject. In a preferred aspect, the pharmaceutical composition comprises at least about 400 mg oritavancin, or a pharmaceutically acceptable salt thereof. In a further preferred aspect, the pharmaceutical composition comprises between about 400 mg to about 1800 mg oritavancin, or a pharmaceutically acceptable salt thereof. In specific aspects, the pharmaceutical composition comprises about 700 mg, 800 mg, 900 mg, 1000 mg, 1100 mg or 1200 mg oritavancin, or a pharmaceutically acceptable salt thereof. In preferred aspects, prevention is maintained is for at least about 24, 72 or 114 hours.

In a variation of this aspect, a single subsequent dose of oritavancin may be administered to the subject. Thus, the method of this embodiment may further comprise administering a second dose of a therapeutically effective amount of a pharmaceutical composition comprising oritavancin, or a pharmaceutically acceptable salt thereof, and a pharmaceutically acceptable carrier or diluent, within the course of therapy. Preferably, the second dose comprises an amount of oritavancin less than or equal to that of the first dose.

Each of the methods of the present invention is preferably practiced wherein the administration of the pharmaceutical compositions is via intravenous administration or oral administration.

The methods of the present invention include those where the bacterial infection is a Complicated Skin and Skin Structure Infection (cSSSI). The methods of the present invention also include those where the infectious bacteria and the bacteria causing a bacterial infection is selected from the group consisting of a gram-positive bacteria, *Staphylococcus aureus*, methicillin-resistant *Staphylococcus aureus*, vancomycin-resistant *Staphylococcus aureus*, vancomycin-intermediate *Staphylococcus aureus*, vancomycin hetero-intermediate *Staphylococcus aureus*, *Streptococcus pyogenes*, *Streptococcus agalactiae*, *Streptococcus anginosus*, *Streptococcus intermedius*, *Streptococcus constellatus*, *Streptococcus dysgalactiae*, *Streptococcus dysgalactiae* subsp. *equisimilis*, *Streptococcus pneumoniae*, Group A *Streptococci* species, Group B *Streptococci* species, Group C *Streptococci* species, Group D *Streptococci* species, *Enterococci* species, *Enterococcus faecalis*, vancomycin-resistant *Enterococcus faecalis*, *Enterococcus faecium*, vancomycin-resistant *Enterococcus faecium*, *Staphylococcus epidermidis*, methicillin-resistant *Staphylococcus epidermidis*, *Staphylococcus haemolyticus*, *Bacillus anthracis* and *Clostridium difficile*.

DETAILED DESCRIPTION OF THE INVENTION

Figure 1:
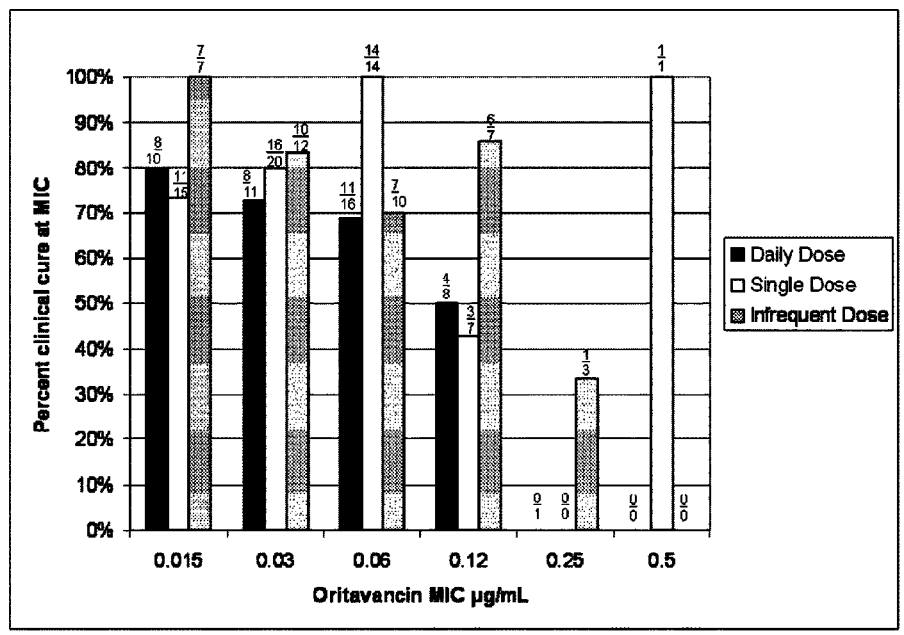
FIG. 1. Clinical cure rates for *Staphylococcus aureus* by oritavancin MIC in the microbiologically evaluable population at test-of-cure.

The present invention is based on the discovery by the inventors that oritavancin exhibits a prolonged plasma half-life. This discovery permits single doses of the compound to be effective in the treatment, prophylaxis or prevention of bacterial infections in a subject. Accordingly, in a first embodiment the present invention is directed to methods of treating a bacterial infection in a subject, comprising administering one dose of a therapeutically effective amount of oritavancin, or a pharmaceutically acceptable salt thereof, over a course of therapy to a subject having a bacterial infection. Specific aspects of this embodiment are provided in the summary of the invention.

In a second embodiment the present invention is directed to methods of providing prophylaxis for a bacterial infection in a subject, comprising administering one dose of a therapeutically effective amount of oritavancin, or a pharmaceutically acceptable salt thereof, over a course of therapy to a subject in need of prophylaxis. Specific aspects of this embodiment are provided in the summary of the invention.

In third embodiment the present invention is directed to methods of preventing a bacterial infection in a subject, comprising administering one dose of a therapeutically effective amount of oritavancin, or a pharmaceutically acceptable salt thereof, over a course of therapy to a subject in need of prevention. Specific aspects of this embodiment are provided in the summary of the invention.

In each embodiment, a second dose of a therapeutically effective amount of oritavancin, or a pharmaceutically acceptable salt thereof, may be administered to the subject.

Preferably, in each embodiment of the invention oritavancin is administered in the form of a pharmaceutical composition comprising oritavancin, or a pharmaceutically acceptable salt thereof, and a pharmaceutically acceptable carrier or diluent.

Oritavancin (also termed N-(4-(4-chlorophenyl)benzyl) A82846B and LY333328) has the following chemical structure:

Oritavancin may be used per se in the methods of the present invention, or in the form of a pharmaceutically acceptable salt, hydrate, solvate, or mixtures thereof. The term "pharmaceutically acceptable salt" refers to non-toxic acid addition salts derived from inorganic and organic acids. While reference is made herein to both "oritavancin" and "a pharmaceutically acceptable salt thereof", the term "oritavancin" should be understood to include both the compound per se as well as a pharmaceutically acceptable salt, unless otherwise indicated by context, as the term "oritavancin" alone may be used for the sake of brevity.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counter-ion forming a part of any salt of this invention is not of a critical nature, so long as the salt as a whole is pharmacologically acceptable and as long as the counter-ion does not contribute undesired qualities to the salt as a whole.

Means for the preparation of the glycopeptide antibiotics, including oritavancin and analogs thereof, may be found, for example, in U.S. Pat. No. 5,840,684, incorporated herein by reference in its entirety.

Pharmaceutical Compositions

In each of the methods of the present invention, oritavancin may be administrated to the subject in the form of a pharmaceutical composition. The pharmaceutical compositions of the invention comprise oritavancin, or a pharmaceutically acceptable salt thereof, and a pharmaceutically acceptable carrier or excipient.

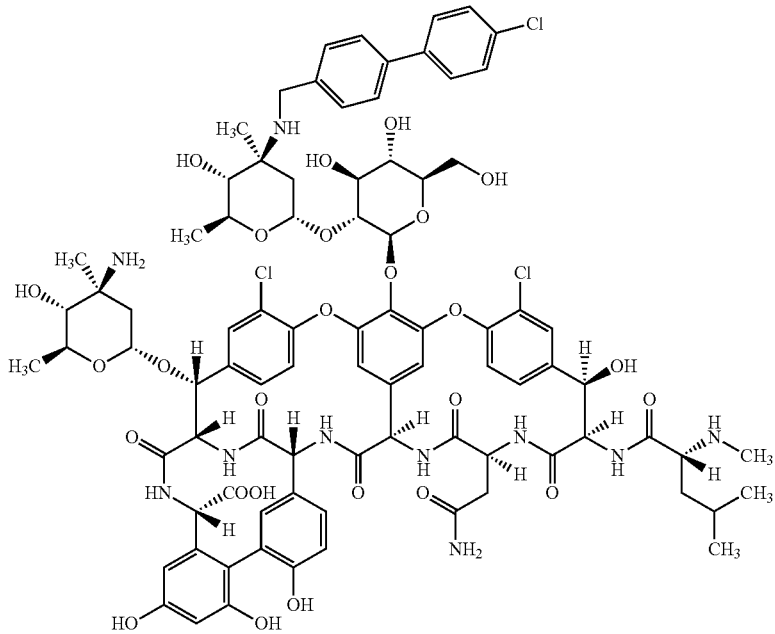 [SMILES: CN[C@H](CC(C)C)C(=O)N[C@H]1C(=O)N[C@@H](CC(N)=O)C(=O)N[C@H]2C(=O)N[C@H]3C(=O)N[C@H](C(=O)N[C@H](C(=O)O)c4cc(O)cc(O)c4-c4cc3ccc4O)[C@H](O[C@H]3C[C@](C)(N)[C@@H](O)[C@H](C)O3)c3ccc(c(Cl)c3)Oc3cc2cc(c3O[C@@H]2O[C@H](CO)[C@@H](O)[C@H](O)[C@H]2O[C@H]2C[C@](C)(NCc3ccc(-c4ccc(Cl)cc4)cc3)[C@@H](O)[C@H](C)O2)Oc2ccc(cc2Cl)[C@H]1O]

Pharmaceutically acceptable carriers and excipient are those compounds, solutions, substances or materials that can be used to produce formulations of oritavancin that are suitable for administered to a subject, such as a human. In particular, carriers and excipients of the present invention are those useful in preparing a pharmaceutical composition that is generally safe, non-toxic and neither biologically nor otherwise undesirable, and that may present pharmacologically favorable profiles, and includes carriers and excipient that are acceptable for veterinary use as well as human pharmaceutical use. Suitable pharmaceutically acceptable carriers and excipients are well known in art and can be determined by those of skill in the art as the clinical situation warrants. The skilled artisan will understand that diluents are included within the scope of the terms carriers and excipients. Examples of suitable carriers and excipients include dextrose, water, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin; see, e.g., U.S. patent application publication 20060194717), hydrophilic and hydrophobic carriers, and combinations thereof. Hydrophobic carriers include, for example, fat emulsions, lipids, PEGylated phospholids, polymer matrices, biocompatible polymers, lipospheres, vesicles, particles, and liposomes. The terms specifically exclude cell culture medium. More particularly: (1) 5% (w/v) dextrose, or (2) water, may be used as a pharmaceutically acceptable carrier.

Excipients included in a formulation have different purposes depending, for example on the nature of the drug, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweeteners, perfuming agents, flavouring agents, coloring agents, administration aids, and combinations thereof.

The compositions may contain common carriers and excipients, such as cornstarch or gelatin, lactose, sucrose, microcrystalline cellulose, kaolin, mannitol, dicalcium phosphate, sodium chloride, alginic acid, croscarmellose sodium, and sodium starch glycolate.

The particular carrier, diluent or excipient used will depend upon the means and purpose for which the active ingredient is being applied.

Pharmaceutically acceptable excipients also include tonicity agents that make the composition compatible with blood. Tonicity agents are particularly desirable in injectable formulations.

Acceptable methods for preparing the pharmaceutical compositions according to the invention are known to those skilled in the art. For example, pharmaceutical compositions may be prepared following conventional techniques of the pharmaceutical chemist involving steps such as mixing, granulating, and compressing when necessary for tablet forms, or mixing, filling, and dissolving the ingredients as appropriate, to give the desired products for various routes of administration.

Methods of Treatment, Prophylaxis and Prevention

The methods of the invention comprise contacting bacteria with an effective amount of oritavancin, or a pharmaceutically acceptable salt thereof. For example, one can inhibit cell wall biosynthesis in a gram-positive bacterium by contacting such a bacterium with oritavancin. The contacting may be carried out in vitro (in biochemical and/or cellular assays), in vivo in a non-human animal, in vivo in mammals, including humans and/or ex vivo (e.g. for sterilization purposes). As used herein, the term "contacting" is meant to broadly refer to bringing a bacterial cell and a molecule of oritavancin into sufficient proximity such that oritavancin can exert an effect on the bacterial cell. Oritavancin may be transported to the location of the bacterial cell, or oritavancin may be situated in a location to which the bacterial cell travels or is brought into contact. The skilled artisan will understand that the term "contacting" includes physical interaction between oritavancin and a bacterial cell, as well as interactions that do not require physical interaction.

As used herein, a "subject" means an animal, such as a mammal, including humans, other higher primates, lower primates, and animals of veterinary importance, such as dogs, cats, horses, sheep, goats, and cattle and the like, preferably a human. The subject may have a bacterial infection, may be at risk for developing a bacterial infection, or may be at greater risk than the general population for exposure to infectious bacteria.

As used herein, "bacterial infection" refers to an infection caused by a species or strain of bacteria for which the single dosing methods disclosed herein are appropriate. For example, the methods of treatment may be used in the treatment of subjects having bacterial skin infections, such as complicated skin and skin structure infections (cSSSI) and complicated and uncomplicated skin and soft tissue infections (SSTI), including abscesses, ulcers, burns and cellulitis. The methods of treatment also include treatment of deep bacterial infections, such as major abscess, infected ulcer, major burn, or deep and extensive cellulitis. Further bacterial infections that may be treated using the methods of the present invention include blood stream infections (BSI), catheter-related blood stream infections (CRBSI), osteomyelitis, prosthetic joint infections, pneumonia (community acquired and nosicomial), joint space infections and device infections (e.g., infections associated with pace makers and internal cardiac defibrillators). The methods of treatment can also be practiced concomitantly with surgical intervention for the bacterial infection.

The infectious bacteria and those bacteria causing bacterial infections include those described in U.S. Pat. No. 5,840,684, gram-positive bacteria, and in particular, *Staphylococcus aureus* (methicillin-susceptible and -resistant strains; vancomycin-susceptible, -intermediate, -hetero-intermediate and -resistant strains), *Streptococcus pyogenes, Streptococcus agalactiae, Streptococcus anginosus* grp. (including *S. anginosus, S. intermedius*, and *S. constellatus*), *Streptococcus dysgalactiae* (including *S. dysgalactiae* subsp. equisimilis), *Streptococcus pneumoniae, Streptococci* species, including *Streptococci* Group A species, *Streptococci* Group B species, *Streptococci* Group C species, and *Streptococci* Group D species, *Enterococci* species, *Enterococcus faecalis* (vancomycin-susceptible and -resistant strains), *Enterococcus faecium* (vancomycin-susceptible and -resistant strains), *Staphylococcus epidermidis* (methicillin-susceptible and -resistant strains), *Staphylococcus haemolyticus, Bacillus anthracis*, and *Clostridium difficile* (both vegetative form and spores).

Methods of Treating

As discussed in the summary of the invention above, in a first embodiment the invention is directed to methods of treating bacterial infections in a subject by administering one dose of oritavancin, or a pharmaceutically acceptable salt thereof, preferably formulated as a pharmaceutical composition, over a course of therapy to a subject. Thus, the invention includes methods of treating a bacterial infection in a subject, comprising administering one dose of a therapeutically effective amount of a pharmaceutical composition comprising oritavancin, or a pharmaceutically acceptable salt thereof, and a pharmaceutically acceptable carrier or diluent, over a course of therapy to a subject having a bacterial infection, thereby treating a bacterial infection in a subject. In an aspect of this embodiment, a second dose of the pharmaceutical composition may be administered to the subject.

The methods of treatment of the present invention may also be based on achieving a particular pharmacokinetic profile for oritavancin in a subject (Bhavnani et al., *Antimicrobial Agents Chemother.* 50(3):994-1000 (2006)). For example, the invention includes methods of treating bacterial infections in a subject, comprising administering one dose of oritavancin, or a pharmaceutically acceptable salt thereof, preferably formulated as a pharmaceutical composition, sufficient to achieve one or more of: (1) a maximum plasma concentration ($C_{max}$) of oritavancin of not less than a selected level, or (2) a minimum area under the concentration curve (AUC 0-24 hr) of at least a selected level.

Thus the invention also includes methods of treating a bacterial infection in a subject, comprising administering one dose of a pharmaceutical composition comprising oritavancin, or a pharmaceutically acceptable salt thereof, and a pharmaceutically acceptable carrier or diluent, over a course of therapy to a subject having a bacterial infection, in an amount sufficient to achieve a maximum plasma concentration ($C_{max}$) of oritavancin of not less than a selected value. In an aspect of this embodiment, a second dose of the pharmaceutical composition may also be administered to the subject.

It will be understood that a therapeutically effective minimum $C_{max}$ of oritavancin will vary based on the concentration of oritavancin in the formulation being administered to a subject, the means of administration, the duration of administration, the type of bacterial infection being treated and the identity of the bacteria in the infection, among other factors such as the physical characteristics of the subject. However, under most circumstances a minimum $C_{max}$ of not less than about 1 μg/mL should be achieved in a subject. Thus, the present invention includes achieving a minimum $C_{max}$ of not less than about 1, 5, 10, 15, 20, 25, 30, 35, 40, 45, 50, 55, 60, 65, 70, 75, 80, 85, 90, 95 or 100 pg/mL in the subject. In preferred aspects, the $C_{max}$ of oritavancin is not less than about 20 μg/mL. In other preferred aspects, the $C_{max}$ of oritavancin is not less than about 40 μg/mL, 60 μg/mL, or 80 μg/mL.

The invention further includes methods of treating a bacterial infection in a subject, comprising administering one dose of a pharmaceutical composition comprising oritavancin, or a pharmaceutically acceptable salt thereof, and a pharmaceutically acceptable carrier or diluent, over a course of therapy to a subject having a bacterial infection, in an amount sufficient to achieve an area under the concentration curve (AUC 0-24 hr) of oritavancin of at least a selected value. In an aspect of this embodiment, a second dose of the pharmaceutical composition may also be administered to the subject.

It will be understood that a therapeutically effective minimum AUC 0-24 hr of oritavancin will vary based on the concentration of oritavancin in the formulation being administered to a subject, the means of administration, the duration of administration, the type of bacterial infection being treated and the identity of the bacteria in the infection, among other factors such as the physical characteristics of the subject. However, under most circumstances a minimum AUC 0-24 hr of at least about 20 μg*h/mL should be achieved in a subject.

Thus, the present invention includes achieving a minimum AUC of not less than about 20, 25, 30, 35, 40, 45, 50, 55, 60, 65, 70, 75, 80, 85, 90, 95, 100, 105, 110, 115, 120, 125, 130, 135, 140, 145 or 150 μg*h/mL in the subject. In preferred aspects, the AUC 0-24 hr of oritavancin is at least about 20 μg*h/mL. In other preferred aspects, the AUC 0-24 hr of oritavancin is at least about 40 μg*h/mL, 80 μg*h/mL, or 120 μg*h/mL.

The terms "treating" and "treatment" mean at least the mitigation of a disease condition or symptom associated with a bacterial infection in a subject that is achieved by a reduction of growth, replication, and/or propagation, or death or destruction of bacteria, on or in the subject. The terms "treating" and "treatment" include curing, healing, inhibiting, relieving from, improving and/or alleviating, in whole or in part, the disease condition. The mitigation of a disease condition or symptom may be about 100%, 99%, 98%, 97%, 96%, 95%, 90%, 80%, 70%, 60%, 50%, 40%, 30%, 20%, 10%, 5% or 1% in the subject, versus a subject to which oritavancin has not been administered. In one aspect, treating means reducing the population of bacteria causing the infection in the subject to an undetectable level, where detection is by any conventional means, such culturing a sample in the laboratory. In another aspect, treating means complete healing of the infection, shown by an absence of clinical symptoms associated with the infection. In further aspect of the invention, treating means the mitigation of a disease condition or symptom by at least about 90% in the subject. In an additional aspect, treating means the mitigation of a disease condition or symptom by at least about 95% in the subject.

The therapeutically effective amount of oritavancin and the amount sufficient to achieve the stated goals of the methods of treatment disclosed herein in each dosage will vary, for example, in view of the physical characteristics of the subject, the severity of the subject's symptoms, the form of the infection, the identity of the bacteria, the formulation and the means used to administer the drug, and the method being practiced. The specific dose for a given subject is usually set by the judgment of the attending physician. However, in each dose a therapeutically effective amount of oritavancin is typically at least about 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 mg oritavancin. In specific aspects, in each dose a therapeutically effective amount of oritavancin is between about 100 mg and 3000 mg oritavancin, preferably about 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 mg oritavancin.

In a preferred aspect, the dose contains at least about 400 mg oritavancin. In a further preferred aspect, the dose contains between about 400 mg to about 1800 mg oritavancin. In specific aspects, the dose contains about 800, 900, 1000, 1100 or 1200 mg oritavancin.

Depending on the means of administration, the dosage may be administered all at once, such as with an oral formulation in a capsule, or slowly over a period of time, such as with an intravenous administration. For slower means of administration, the administering period can be a matter of minutes, such as about 5, 10, 15, 20, 25, 30, 35, 40, 45, 50, 55, 60, 65, 70, 75, 80, 85, 90, 95, 100, 105, 110, 115, 120 or more minutes, or a period of hours, such as about 0.5, 1, 1.5, 2, 2.5, 3, 3.5, 4, 4.5, 5 or more hours. The administration of the dose may be interrupted, such as where the dose is administered via intravenous infusion and the dose is divided into two or more infusion bags. Under such circumstances, the administration of the dose may be interrupted while the infusion bags are changed.

Methods of Prophylaxis

In a second embodiment, the invention is directed to methods of providing prophylaxis for bacterial infections in a subject by administering one dose of oritavancin, or a pharmaceutically acceptable salt thereof, preferably formulated as a pharmaceutical composition over a course of therapy to a subject. Thus, the invention includes a method of providing prophylaxis for a bacterial infection in a subject, comprising administering one dose of a therapeutically effective amount of a pharmaceutical composition comprising oritavancin, or a pharmaceutically acceptable salt thereof, and a pharmaceutically acceptable carrier or diluent, over a course of prophylaxis to a subject at risk of developing a bacterial infection, thereby providing prophylaxis for a bacterial infection in a subject. In an aspect of this embodiment, a second dose of the pharmaceutical composition may be administered to the subject.

Many physicians believe that humans should be considered for antibiotic prophylaxis before a surgical procedure, a dental procedure or invasive medical procedure to mitigate the potential for an infection resulting from ineffective sterility during the procedure. Deep infection is a serious complication sometimes requiring subsequent medical interventions and is accompanied by significant morbidity and mortality. Oritavancin may therefore be used as a replacement for, or in addition to, prophylactic antibiotics in this situation. For instance, oritavancin and/or pharmaceutical compositions of the invention may be administered to a subject to achieve a systemic and/or local effect against relevant bacteria shortly before an invasive medical treatment, such as surgery or insertion of an in-dwelling device (e.g. joint replacement (hip, knee, shoulder, etc.)). Treatment may be repeated after the invasive medical treatment, such as post-operatively or during the in-body time of the device.

The term "prophylaxis" means a reduction in the likelihood that a disease condition associated with a bacterial infection will develop in a subject, preferably a human. In particular, the term is related to the administration of oritavancin to a subject to reduce the likelihood of the occurrence of a bacterial infection, such as bacterial infection that may occur during or following a surgery, a dental procedure or invasive medical procedure. For example, one can reduce the likelihood of a bacterial infection in a subject by administering oritavancin before exposure to bacteria. The prophylaxis may be about a reduction of at least about 100%, 99%, 98%, 97%, 96%, 95%, 90%, 80%, 70%, 60%, 50%, 40%, 30%, 20%, 10%, 5% or 1% in the subject, versus a subject to which oritavancin has not been administered. The prophylaxis may last in the subject for at least about 0.5, 1, 2, 3, 4, 5, 6, 7, 8, 9, 10, 11, 12, 13, 14, 15, 16, 17, 18, 19, 20, 22, 23 or 24 hours, or 2, 3, 4, 5, 6, 7, 8, 9, 10, 12, 14, 16, 18, 20, 22, 24, 26, 28, 30 or more days after administration of oritavancin. In an alternative aspect, prophylaxis is maintained for the duration of a surgical procedure, a dental procedure or an invasive medical procedure.

In preferred aspects, prophylaxis (i.e., a reduction in the likelihood that a disease condition associated with a bacterial infection will develop in a subject) is maintained for at least about 4, 8 or 12 hours. In one particular aspect, the reduction in the likelihood that a disease condition associated with a bacterial infection will develop in a subject is a reduction of at least about 90% for at least about 4 hours. In another particular aspect, the reduction in the likelihood that a disease condition associated with a bacterial infection will develop in a subject is a reduction of at least about 95% for at least about 4 hours.

Oritavancin or a pharmaceutical composition comprising the compound may be administered within 10, 9, 8, 7, 6, 5, 4, 3, 2, or 1 day, or within 24, 22, 20, 18, 16, 14, 12, 10, 9, 8, 7, 6, 5, 4, 3, 2, 1 or 0.5 hour prior to when a subject will potentially be exposed to bacteria, such a prior to surgery or a dental procedure, thereby permitting an advisable systemic or local presence of oritavancin, preferably in the areas potentially exposed to bacterial contamination during the surgical procedure.

The therapeutically effective amount of oritavancin in each dosage for prophylaxis will vary depending, for example, upon the physical characteristics of the subject, the procedure to which the subject will be subjected, the identity of the bacteria that could potentially cause infection, the formulation and the means used to administer the drug. The specific dose for a given subject is usually set by the judgment of the attending physician. However, in each dose a therapeutically effective amount of oritavancin is typically at least about 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 mg oritavancin. In specific aspects, in each dose a therapeutically effective amount of oritavancin is between about 100 mg and 3000 mg oritavancin, preferably about 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 mg oritavancin.

In a preferred aspect, the dose contains at least about 200 mg oritavancin. In a further preferred aspect, the dose contains between about 200 mg to about 1800 mg oritavancin. In specific aspects, the dose contains about 300, 400, 500, 600, 700 or 800 mg oritavancin.

Depending on the means of administration, the dosage may be administered all at once, such as with an oral formulation in a capsule, or slowly over a period of time, such as with an intravenous administration. For slower means of administration, the administering period can be a matter of minutes, such as about 5, 10, 15, 20, 25, 30, 35, 40, 45, 50, 55, 60, 65, 70, 75, 80, 85, 90, 95, 100, 105, 110, 115, 120 or more minutes, or a period of hours, such as about 0.5, 1, 1.5, 2, 2.5, 3, 3.5, 4, 4.5, 5 or more hours. The administration of the dose may be interrupted, such as where the dose is administered via intravenous infusion and the dose is divided into two or more infusion bags. Under such circumstances, the administration of the dose may be interrupted while the infusion bags are changed.

Methods of Preventing

In a third embodiment, the invention is directed to methods of preventing bacterial infections in a subject by administering one dose of oritavancin, or a pharmaceutically acceptable salt thereof, preferably formulated as a pharmaceutical composition, over a course of therapy to a subject. Thus, the invention includes a method of preventing a bacterial infection in a subject, comprising administering one dose of a therapeutically effective amount of a pharmaceutical composition comprising oritavancin, or a pharmaceutically acceptable salt thereof, and a pharmaceutically acceptable carrier or diluent, over a course of prevention to a subject at risk of exposure to infectious bacteria, thereby preventing a bacterial infection in a subject. In an aspect of this embodiment, a second dose of the pharmaceutical composition may be administered to the subject.

The terms "prevent" and "prevention" mean blocking or stopping a disease condition associated with a bacterial infection from developing in a subject, preferably a human. Such methods may be practiced, for example, on subjects having a higher risk for bacterial infection than the general population, including patients undergoing treatment for bacterial infections whereby normal gut flora is inhibited by antimicrobial therapy, patients with impaired immune function (e.g., immunoglobulin deficiency, splenic dysfunction, splenectomy, HIV infection, impaired leukocyte function, hemoglobinopathies), the elderly (Loo et al., 2005. NEJM 353:2442), people with certain malignancies (e.g., multiple myeloma, chronic lympocytic leukemia, lymphoma), people at increased occupational risk (e.g., public services workers, such a fire, water, sanitary, police, medical, and laboratory workers, hospital workers), people in closed populations (e.g., prisons, military, nursing homes) and others that have immunological deficiencies that might enhance their susceptibility to bacterial infection. The prevention may last in the subject for at least about 0.5, 1, 2, 3, 4, 5, 6, 7, 8, 9, 10, 11, 12, 13, 14, 15, 16, 17, 18, 19, 20, 25, 30, 35, 40, 45, 50 or more days after administration of oritavancin.

In one aspect of the invention, the prevention lasts at least about 24 hours in the subject. In another aspect, the prevention lasts at least about 72 hours in the subject. In further aspect, the prevention lasts at least about 144 hours in the subject.

Oritavancin or a pharmaceutical composition comprising the compound may be administered within 10, 9, 8, 7, 6, 5, 4, 3, 2, or 1 day, or within 24, 22, 20, 18, 16, 14, 12, 10, 9, 8, 7, 6, 5, 4, 3, 2, 1 or 0.5 hour prior to when a subject will potentially be exposed to bacteria, such prior to contact by military personnel with a material suspected of containing a particular bacteria.

The therapeutically effective amount of oritavancin in each dosage for prevention will vary depending, for example, upon the physical characteristics of the subject, the identity of the bacteria to which the subject may be exposed, the formulation and the means used to administer the drug. The specific dose for a given subject is usually set by the judgment of the attending physician. However, in each dose a therapeutically effective amount of oritavancin is typically at least about 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 mg oritavancin. In specific aspects, in each dose a therapeutically effective amount of oritavancin is between about 100 mg and 3000 mg oritavancin, preferably about 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 mg oritavancin.

In a preferred aspect, the dose contains at least about 400 mg oritavancin. In a further preferred aspect, the dose contains between about 400 mg to about 1800 mg oritavancin. In specific aspects, the dose contains about 700, 800, 900, 1000, 1100 or 1200 mg oritavancin.

Depending on the means of administration, the dosage may be administered all at once, such as with an oral formulation in a capsule, or slowly over a period of time, such as with an intravenous administration. For slower means of administration, the administering period can be a matter of minutes, such as about 5, 10, 15, 20, 25, 30, 35, 40, 45, 50, 55, 60, 65, 70, 75, 80, 85, 90, 95, 100, 105, 110, 115, 120 or more minutes, or a period of hours, such as about 0.5, 1, 1.5, 2, 2.5, 3, 3.5, 4, 4.5, 5 or more hours. The administration of the dose may be interrupted, such as where the dose is administered via intravenous infusion and the dose is divided into two or more infusion bags. Under such circumstances, the administration of the dose may be interrupted while the infusion bags are changed.

Second Dose

Under some circumstances, a second dose of oritavancin may be required to be administered to achieve the goal of a given method. For example, an attending physician may determine that one dose of oritavancin has not been sufficient to achieve full treatment of a particular bacterial infection in a patient.

When a second dose is administered to a subject within the course of therapy, preferably the amount of oritavancin in the second dose is the same as or less than the amount administered to the patient in the first dose. In specific embodiments, the amount of oritavancin in the second dose is 100% or less, 90% or less, 80% or less, 70% or less, 60% or less, 50% or less, 40% or less, 30% or less, 20% or less, or 10% or less than the amount of oritavancin in the first dose.

When a second dose is administered over the course of therapy, the delay between doses will vary based on the same considerations discussed herein concerning the amount of oritavancin to be included in a dose. The delay can be determined by the attending physician. In general however, when the method being practiced is a method of treatment, the delay between the doses may be about 0.5, 1, 1.5, 2, 2.5, 3, 3.5, 4, 4.5, 5, 5.5, 6, 6.5, 7, 7.5, 8, 8.5, 9, 9.5 or 10 days, preferably about 4 days. When the method being practiced is a method of prophylaxis, the delay between the doses may be about 0.5, 1, 1.5, 2, 2.5, 3, 3.5, 4, 4.5, 5, 5.5, 6, 6.5, 7, 7.5, 8, 8.5, 9, 9.5 or 10 hours. When the method being practiced is a method of prevention, the delay between the doses may be about 1, 1.5, 2, 2.5, 3, 3.5, 4, 4.5, 5, 5.5, 6, 6.5, 7, 7.5, 8, 8.5, 9, 9.5 or 10 days.

Where two or more doses of oritavancin are being administered over the course of therapy, the individual doses may be administered in the same manner and/or formulation, or in different manners and/or formulations.

As used herein, the terms "dose", "unit dose", "dosage", "effective dose" and related terms refer to physically discrete units that contain a predetermined quantity of active ingredient calculated to produce a desired therapeutic effect. A single dose is thus a predetermined quantity of oritavancin that is administered to a subject. Preferably, as disclosed in the methods of the invention, the oritavancin is formulated as a pharmaceutical composition for administration to the subject.

As used herein, the term "course of therapy" depends on the particular method of the invention, however the term generally means the period of time within which or over which a selected goal is achieved. In terms of methods of treatment, the course of therapy is the time period which is required to achieve treatment of the bacterial infection in the subject. In terms of methods of prophylaxis, the course of therapy is the period of time over which prophylaxis for a bacterial infection is achieved. In terms of methods of prevention, the course of therapy is the period of time over which prevention from a bacterial infection is achieved.

Although the invention is preferably directed to the treatment, prevention and/or prophylaxis of bacterial infections, the invention encompasses therapeutic and prophylactic methods against other diseases caused by or related to bacterial infection, including but not limited to otitis, conjunctivitis, pneumonia, bacteremia, sinusitis, pleural empyema and endocarditis, intravascular or endothelial infections, osteomyelitis and meningitis. In such methods, one dose of oritavancin is administered to a subject in an amount sufficient to provide a therapeutic effect and thereby prevent or treat the infection of the subject.

The pharmaceutical compositions and compounds of the present invention may be formulated, for example, for oral, enteral, sublingual, intranasal, intraocular, rectal, intravaginal, transdermal, mucosal, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedullary, intracardiac, intra-articular (joint), intrasynovial (joint fluid area), intracranial, intraspinal, and intrathecal (spinal fluids). Any known device useful for parenteral injection or infusion of drug formulations can be used to effect such administration.

For topical use, the pharmaceutical compositions of present invention can be prepared in suitable forms to be applied to the skin, or mucus membranes of the nose and throat, vagina or rectum, and can take the form of creams, ointments, suppositories, nasal drops, liquid sprays or inhalants, lozenges, or throat paints. Such topical formulations further can include chemical compounds such as dimethylsulfoxide (DMSO) to facilitate surface penetration of the active ingredient. For application to the eyes or ears, the pharmaceutical compositions can be presented in liquid or semi-liquid form formulated in hydrophobic or hydrophilic bases as ointments, creams, lotions, paints or powders. For rectal administration the pharmaceutical compositions can be administered in the form of suppositories admixed with conventional carriers such as cocoa butter, wax or other glyceride.

Formulations for parenteral administration can be in the form of aqueous or non-aqueous isotonic sterile solutions, suspensions or fat emulsions. The unit dosage of these solutions or suspensions can be in a concentrated liquid, powder or granular form for ex tempore reconstitution in the appropriate pharmaceutically acceptable carrier, such as sterile water, at the time of delivery. In addition to the above-mentioned excipients, powder forms optionally include bulking agents (e.g. mannitol, glycine, lactose, sucrose, trehalose, dextran, hydroxyethyl starch, ficoll and gelatin), and cryo or lyoprotectants. In an alternative embodiment, the parenteral unit dosage form of pharmaceutical compositions and compounds of the present invention can be a ready-to-use solution of the pharmaceutical compositions and compounds in a suitable carrier in sterile, hermetically sealed ampoules or in sterile pre-loaded syringes. The suitable carrier optionally comprises any of the above-mentioned excipients. The parenteral form used for injection must be fluid to the extent that easy syringability exists.

Excipients used in parenteral preparations may also include, without limitation, stabilizing agents (e.g. carbohydrates, amino acids and polysorbates, such as 5% dextrose), solubilizing agents (e.g. cetrimide, sodium docusate, glyceryl monooleate, polyvinylpyrolidone (PVP) and polyethylene glycol (PEG)), surfactants (e.g. polysorbates, tocopherol PEG succinate, poloxamer and Cremophor™), buffers (e.g. acetates, citrates, phosphates, tartrates, lactates, succinates, amino acids and the like), antioxidants and preservatives (e.g. BHA, BHT, gentisic acids, vitamin E, ascorbic acid, sodium ascorbate and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vaso-constrictors for prolongation and agents that increase tissue permeability), and combinations thereof.

Parenteral formulations using hydrophobic carriers include, for example, fat emulsions and formulations containing lipids, liposheres, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

In intravenous (IV) use, a sterile formulation of the pharmaceutical compositions of the present invention and optionally one or more additives, including solubilizers or surfactants, can be dissolved or suspended in any of the commonly used intravenous fluids and administered by infusion. Intravenous fluids include 5% dextrose in water.

In intramuscular preparations, a sterile formulation of the pharmaceutical compositions of the present invention can be dissolved and administered in a pharmaceutical diluent such as Water-for-Injection (WFI) or 5% dextrose in water. A suitable insoluble form of the pharmaceutical compositions may be prepared and administered as a suspension in an aqueous base or a pharmaceutically acceptable oil base, e.g. an ester of a long chain fatty acid such as ethyl oleate.

For oral use, the oral pharmaceutical composition may be made in the form of a unit dosage containing a therapeutically-effective amount of the pharmaceutical compositions. Solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, tablets, capsules, suspensions or liquid syrups or elixirs, wafers and the like. For general oral administration, excipient or additives include, but are not limited to inert diluents, fillers, disintegrating agents, binding agents, wetting agents, lubricating agents, sweetening agents, flavoring agents, coloring agents and preservatives.

The tablets and capsules can contain, in addition to the glycopeptide antibiotics, conventional carriers such as: inert diluents (e.g., sodium and calcium carbonate, sodium and calcium phosphate, and lactose), binding agents (e.g., acacia gum, starch, gelatin, sucrose, polyvinylpyrrolidone (Povidone), sorbitol, tragacanth methylcellulose, sodium carboxymethylcellulose, hydroxypropyl methylcellulose, and ethylcellulose), fillers (e.g., calcium phosphate, glycine, lactose, maize-starch, sorbitol, or sucrose), wetting agents, lubricating agents (e.g., metallic stearates, stearic acid, polyethylene glycol, waxes, oils, silica and colloical silica, silicon fluid or talc), disintegrating agents (e.g., potato starch, corn starch and alginic acid), flavouring (e.g. peppermint, oil of wintergreen, fruit flavoring, cherry, grape, bubblegum, and the like), and coloring agents. Carriers may also include coating excipients such as glyceryl monostearate or glyceryl distearate, to delay absorption in the gastrointestinal tract.

Oral liquid preparations, generally in the form of aqueous or oily solutions, suspensions, emulsions or elixirs, may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, microcrystalline cellulose, methyl or propyl para-hydroxybenzoate, propylene glycol, sorbitol, or sorbic acid. In one embodiment, the compounds may be formulated in 10% hydroxypropyl beta-cyclodextrin. In a further embodiment the compounds may be formulated in 85% polyethylene glycol 400 (PEG400) in sterile water. The oral formulation may be in the form of a liquid to be drunk by the subject, in the form of a capsule containing the formulation, or other means known to the skilled artisan for administering an oral formulation.

While the treatment can be administered in a systemic manner through the means described above, it may also be administered in a localized manner. For example, the treatment may be administered directly, such as through a topical composition or directly into a subcutaneous or other form of wound.

Each of the methods of the present invention may also be practiced by administering a second therapeutic agent to the subject. Such second therapeutic agents may be included in a pharmaceutical formulation comprising oritavancin, or they may be administered separately. A wide range of second therapeutic agents, such as antibiotics, can be used in combination with the compounds, compositions and methods of the present invention. Antibiotics used as second therapeutic agents may act by interfering with cell wall synthesis, plasma membrane integrity, nucleic acid synthesis, ribosomal function, folate synthesis, etc. A non-limiting list of useful antibiotics includes: fusidic acid, trimethoprim, sulfadiazine, sulfamethoxazole, a penicillin, a monobactam, a penam, a penem, a clavam, a clavem, a carbopenam, a carbopenem, a cepham, a cephem, an oxacepham, an oxacephem, a carbocepham, a carbocephem, a cephalosporin, tetracycline, a tetracycline derived antibacterial agent, glycylcycline, a glycylcycline derived antibacterial agent, minocycline, a minocycline derived antibacterial agent, sancycline, a sancycline derived antibacterial agent, methacycline, a methacycline derived antibacterial agent, an oxazolidinone antibacterial agent, an aminoglycoside antibacterial agent, an additional glycopeptide or lipoglycopeptide, a quinolone antibacterial agent, daptomycin, a daptomycin derived antibacterial agent, rifamycin, a rifamycin derived antibacterial agent, rifampin, a rifampin derived antibacterial agent, rifalazil, a rifalazil derived antibacterial agent, rifabutin, a rifabutin derived antibacterial agent, rifapentin, a rifapentin derived antibacterial agent, rifaximin and a rifaximin derived antibacterial agent.

The second therapeutic agent may be administered before, concurrently with, or after a pharmaceutical formulation of the present invention is administered to a subject.

The present invention also includes a kit comprising one or two doses of a pharmaceutical composition comprising oritavancin and written instructions for its use in treatment, prophylaxis and/or prevention of a bacterial infection, in a suitable container.

EXAMPLES

Example 1

Oritavancin (Ori) is a semisynthetic lipoglycopeptide with demonstrated efficacy against gram-positive cSSSI including MRSA, when given 200 mg IV daily for 3-7 days (D) in a multi-dose (MD) fashion. Animal & phase 2 & 3 PK data suggest potential for single dose (SD) or infrequent doses (ID) of Ori as potentially efficacious for cSSSI.

A phase 2, multi-center, randomized, double-blind, parallel, active-comparator study in which three dose regimens of oritavancin were explored as a treatment for cSSSI due to gram-positive pathogens was conducted using: a daily dose (200 mg) administered for three to seven days, a single dose (1200 mg), and an infrequent dose (800 mg dose with option for an additional 400 mg on Day 5).

Study Design and Treatment.

Patients were randomized through an interactive voice response system in a 1:1:1 ratio to receive either 1) oritavancin comparator daily dose: 200 mg IV daily for 3 to 7 days as determined by the investigator based on clinical criteria, 2) oritavancin single dose: 1200 mg oritavancin IV on Day 1, or; 3) oritavancin infrequent dose: 800 mg IV on Day 1 with optional 400 mg IV on Day 5 as determined by investigator based on clinical criteria. During randomization patients were stratified by disease categories of wound infection, major abscess, and cellulitis. Placebo IV (5% dextrose in water) was given to maintain the blind.

Inclusion and Exclusion Criteria.

Patients were enrolled in the study if they had a cSSSI, presumed or proven to be caused by gram-positive pathogen(s), that met disease diagnostic criteria (listed below and separated by disease state), were $\geq 18$ years of age, and had a body mass index $\geq 17$ kg/m$^2$ and $\leq 40$ kg/m$^2$.

For the skin and skin structure infection to be classified as complicated one or more of the following criteria had to be met: 1) infection required significant surgical intervention within 48 hours before or after enrollment; 2) infection process was suspected or confirmed to involve deeper soft tissue, not fascia and/or muscle layers, or; 3) significant underlying disease was present that complicated the response to treatment including, but not limited to diabetes mellitus, bacteremia, corticosteroid therapy or any levels of neutropenia.

Additional criteria had to be met for each of the three categories of infection (wound infection, major abscess, cellulitis). Wound infections must have had purulent drainage from the wound or ulcer, but not from the organ/space component of the injury and one or more of the following: systemic manifestation of infection with fever (>38° C.) or leukocytosis (WBC >10,000/mm$^3$ or a differential count showing >10% band forms); localized pain or tenderness; erythema; or localized swelling. Major abscesses must have had acute onset within 7 days prior to enrollment, purulent drainage or purulent aspirate, systemic manifestations of infection with fever or leukocytosis; erythema or induration ($\geq 2$ cm in diameter) or tenderness; and evidence of loculated fluid by physical examination, blind aspiration, or ultrasound that required intervention (e.g., aspiration, incision and drainage, excision) within 48 hours of enrollment. Cellulitis must have had acute onset within 7 days prior to enrollment; pain or tenderness; cutaneous erythema; advancing edema or induration; and history of fever within 3 days prior to enrollment.

Patients were excluded from the study if they received any systemic antimicrobial agent with gram-positive coverage for more than 24 hours within the 3 days prior to enrollment (unless the gram-positive pathogen was resistant in vitro to the antimicrobial agent or the patient was clinically failing on prior therapy), had a history of severe hypersensitivity reactions to glycopeptides and any of their excipients (patients who had histamine-like infusion reactions to the glycopeptide vancomycin were not excluded) or had an anticipated need for more than 10 days of conventional antibiotic therapy. Pregnant women or women who were nursing were also excluded from the study.

Analysis Populations.

Analyses were performed on four patient populations: intent-to-treat (ITT), modified intent-to-treat (MITT), clinically evaluable (CE) and microbiologically evaluable (ME). The ITT population included patients who were randomized to treatment and received any amount of study medication. Two patients who were potentially unblinded were excluded from the ITT population for all efficacy analyses. The MITT population included all ITT patients with a gram-positive pathogen isolated at baseline. The CE population included efficacy ITT patients who met enrollment criteria, received ≧80% of the intended study drug dose in the intended timeframe based on assignment to treatment group, did not have a clinical response of indeterminate at the end-of therapy or first follow-up assessment, had a first follow-up assessment of cure, failure, or improvement, or had a clinical response of failure at end-of-therapy. Patients in the ME population were CE patients who had a gram-positive pathogen isolated at baseline.

Clinical and Microbiologic Assessments.

The primary efficacy endpoint was the clinical response in the CE population at TOC, which occurred 20 to 28 days after study enrollment on Day 1. Clinical response was determined by the investigator as part of the end-of-therapy, TOC, and late follow-up procedures by assessing signs and symptoms including fever, pain, tenderness, erythema, induration, edema, purulent drainage, eschar, and devitalized tissue. A clinical response of cure, improvement, failure, or indeterminate was assigned at end-of-therapy and TOC by the investigator based on clinical signs and symptoms. At late follow-up, the investigator could assign the clinical response of relapse in addition to cure, improvement, or indeterminate. Only patients with a clinical response of cure or improvement at TOC were assessed for clinical response at late follow-up.

Cure was defined as resolution of purulent drainage, pain, edema, fever, erythema, tenderness, and induration. Serous drainage or aspirate and/or granulation tissue could be present. Improvement was defined as resolution of purulent drainage and, in the case of cellulitis, cessation of fever and pain. Residual erythema, edema, pain (in the case of wound or abscess), tenderness, and/or induration could be present as could serous drainage, granulation tissue, eschar, and/or devitalized tissue. Failure included any of the following: presence of purulent drainage (or aspirate) and/or fever; the unanticipated need for abscess drainage or removal of sutures (for treatment of infection)>48 hours after initiation of study therapy; or treatment with nonstudy systemic antibiotic having activity against gram-positive pathogen(s) for the primary infection site or use of topical antibiotics at the site of primary infection 24 hours or more after initiation of study medication therapy.

Blood and infection site cultures were obtained within three days of enrollment (often done at the time of enrollment). End-of-therapy, TOC, and late follow-up (or at early relapse) cultures were obtained from the infection site if clinically indicated. If a patient proved to have bacteremia at baseline, follow-up blood cultures were performed at a minimum at end-of-therapy and TOC. Specimens were cultured and pathogens were identified at each investigative site's certified laboratory. All isolated gram-positive pathogen(s) that were obtained from the infection site at baseline/randomization and up to and including the TOC time point were subcultured and sent to a central laboratory (Covance Clinical Laboratories, Indianapolis, Ind.) for confirmatory identification and susceptibility testing. In cases of discrepancy between the local and the central laboratory, central laboratory results were used.

Statistical Analysis.

The primary hypothesis was that oritavancin single or infrequent doses were non-inferior to oritavancin daily doses. The primary efficacy endpoint was clinical response (either cure or improvement versus failure) at TOC in the CE population. The primary efficacy analyses were a comparison of the proportions of CE patients with a clinical response of cure (defined as investigator assessment of cure or improvement) in the daily dose group compared to, 1) the single dose group and 2) the infrequent dose group. Adjusted estimates for the differences in response rates and the corresponding confidence intervals (CI) were constructed using the Mantel-Haenszel method stratified by disease category.

The designed study used a sample size that was calculated assuming a 2-sided 90% confidence interval for the difference in response rates at 85% with a 15% non-inferiority margin at 80% power. Using these assumptions, a total of 210 clinically evaluable patients (70 per arm) were needed. Assuming an evaluability rate of 70%, 300 total patients (100 per arm) needed to be enrolled to obtain 210 CE patients.

Results

Patients.

A total of 302 patients were randomized and received study medication (100 in the daily dose, 99 in the single dose, and 103 in the infrequent dose groups) with 228 (75.5%) of these patients being clinically evaluable (Table 1). Two patients in the ITT population were potentially unblinded prior to completing the study. These two patients were not included in any efficacy populations, but were included in all safety analyses. In the ITT population, 88.9% of patients in the single dose group, 86.4% of patients in the infrequent dose group, and 89.0% of patients in the daily dose group completed IV therapy. In the ITT population there were 96 patients with wound infections (19 surgical, 47 trauma, 1 infected burn and 29 skin ulcers), 114 with major abscesses, and 92 with cellulitis. Demographics and baseline characteristics were comparable between the three dosing regimens (Table 2).

TABLE 1

| Patient Population | Oritavancin 200 mg N = 100 | Oritavancin 1200 mg N = 99 | Oritavancin 800 mg | | | Total N = 302 |
| --- | --- | --- | --- | --- | --- | --- |
| | | | All N = 103 | 800 mg N = 34 | 800/400 mg N = 69 | |
| | | | n (%) | | | |
| Intent-to-Treat[a] | 98 (98) | 99 (100) | 103 (100) | 34 (100) | 69 (100) | 300 (99.3) |
| Clinically Evaluable | 76 (76) | 81 (81.8) | 71 (68.9) | 23 (67.6) | 48 (69.6) | 228 (75.5) |
| Modified Intent-to-Treat | 72 (72) | 68 (68.7) | 69 (67.0) | 18 (52.9) | 51 (73.9) | 209 (69.2) |
| Microbiologically Evaluable | 55 (55) | 58 (58.6) | 48 (46.6) | 11 (32.4) | 37 (53.6) | 161 (53.3) |

[a]Two patients in the intent-to-treat population were unblinded prior to completing the study. These two patients were not included in any efficacy populations, but were included in all safety analyses

TABLE 2

| Characteristic | Oritavancin 200 mg N = 98 | Oritavancin 1200 mg N = 99 | Oritavancin 800 mg N = 103 |
|---|---|---|---|
| Male patients | 70 (71.4) | 64 (64.6) | 64 (62.1) |
| Age, median (range), years | 47.0 (18-87) | 46 (18-94) | 45 (18-86) |
| Weight, mean ± SD, kg | 75.6 ± 19.0 | 77.8 ± 18.1 | 76.2 ± 18.2 |
| Race | | | |
| Caucasian | 64 (65.3) | 65 (65.7) | 61 (59.2) |
| Asian | 22 (22.4) | 22 (22.2) | 27 (26.2) |
| African descent | 5 (5.1) | 5 (5.1) | 12 (11.7) |
| Other[a] | 7 (7.1) | 7 (7.1) | 3 (2.9) |
| Co-morbid conditions | | | |
| Diabetes | 13 (13.3) | 15 (15.2) | 22 (21.4) |
| Impaired renal function (estimated creatinine clearance ≦50 mL/min)[b] | 7/97 (7.2) | 6/97 (6.2) | 4/102 (3.9) |
| Disease category | | | |
| Wound infection | 32 (32.7) | 30 (30.3) | 34 (33.0) |
| Major abscess | 36 (36.7) | 39 (39.4) | 38 (36.9) |
| Cellulitis | 30 (30.6) | 30 (30.3) | 31 (30.1) |
| Clinical sign | | | |
| Fever (>38° C) | 22 (22.4) | 27 (27.3) | 20 (19.4) |
| White blood cell count >10,000/mm$^3$ | 45 (45.9) | 38 (38.4) | 49 (47.6) |
| Deepest tissue involved | | | |
| Skin | 4 (4.1) | 3 (3.0) | 6 (5.8) |
| Subcutaneous | 82 (83.7) | 85 (85.9) | 86 (83.5) |
| Muscle | 1 (1.0) | 0 | 1 (1.0) |
| Fascial Plane | 7 (7.1) | 5 (5.1) | 9 (8.7) |
| Other | 4 (4.1) | 6 (6.1) | 1 (1.0) |
| Duration of disease, mean ± SD, days | 2.5 (5.27) | 1.9 (1.34) | 2.9 (6.38) |
| Concomitant antibacterial therapy used for primary cSSSI | | | |
| Aztreonam | 7 (7.1) | 3 (3.0) | 7 (6.8) |
| Metronizadole | 8 (8.2) | 3 (3.0) | 12 (11.7) |

Note:
data are n (%) of patients unless otherwise indicated
[a]Other included mixed-racial parentage, American Indian, Alaska native, Native Hawaiian or other Pacific Islander
[b]Estimated creatinine clearance was calculated using the Cockcroft-Gault formula and baseline serum creatinine Baseline Pathogens and Susceptibility.

At least one gram-positive organism was isolated from the infection site at baseline in 209 patients (69.2%) in the ITT population. The most commonly isolated pathogen was *S. aureus*, which was isolated from 87.6% (183/209) of MITT patients. MRSA was isolated in 49% (103/209) of MITT patients. The other three most common pathogens identified in the MITT population were *Streptococcus pyogenes* (5.7%, 12/209), *Streptococcus agalactiae* (3.8%, 8/209) and *Enterococcus faecalis* (3.8%, 8/209). The range of oritavancin minimum inhibitory concentrations (MICs) for *S. aureus* in the MITT population, as assessed using broth microdilution with 0.002% polysorbate-80, was 0.008 to 0.5 μg/mL. The oritavancin MIC$_{90}$ for all *S. aureus* and for the MSSA and MRSA subsets was 0.12 μg/mL.

Clinical Efficacy.

Oritavancin single and infrequent doses demonstrated non-inferiority to oritavancin daily dose with clinical cure rates at TOC in the CE population of 72.4% (55/76), 81.5% (66/81), and 77.5% (55/71) in the daily dose, single dose, and infrequent dose groups, respectively (Table 3). The estimated difference in cure rates along with 90% CIs between the single and daily dose groups was 8.6% (−2.5, 18.2) and between the infrequent and daily dose groups was 5.2% (−6.8, 15.4) demonstrating non-inferiority of the single and infrequent dose regimens. Clinically evaluable patients in the infrequent dose group who only received 800 mg on Day 1 (23/71) and those who received 800 mg on Day 1 plus the optional 400 mg dose on Day 5 (48/71) had cure rates of 78.3% (18/23) and 77.1% (37/48), respectively, which were comparable to overall cure rates. Cure rates by disease category were comparable between all treatment groups for wound infection and major abscess and between the infrequent and daily dose of patients with cellulitis (Table 3). A statistically higher cure rate (90% CI; 9.2, 49.1) was seen for patients with cellulitis in the single dose group (87.5%) compared to the daily dose group (58.3%). More patients with cellulitis who failed in the daily dose group had unplanned surgical procedures or interventions (4/14, 29%) than in the single (0/9) or infrequent dose groups (1/14, 7%).

TABLE 3

| Response | Oritavancin 200 mg N = 98[a] | Oritavancin 1200 mg N = 99 | Oritavancin 800 mg N = 103 | Estimated Difference[b] 1200 mg – 200 mg (90% CI) | Estimated Difference[b] 800 mg – 200 mg (90% CI) |
|---|---|---|---|---|---|
| | | % (n of patients/total) | | | |
| Intent to treat | | | | | |
| Cure | 72.4 (63/87) | 81.8 (72/88) | 78.2 (68/87) | 8.7 (−1.7, 17.8) | 5.1 (−5.8, 14.6) |
| Clinically evaluable | | | | | |
| Cure | 72.4 (55/76) | 81.5 (66/81) | 77.5 (55/71) | 8.6 (−2.5, 18.2) | 5.2 (−6.8, 15.4) |
| Clinically evaluable cure rates by disease category | | | | | |
| Wound | 65.4 (17/26) | 66.7 (18/27) | 72.0 (18/25) | 1.3 (−20.1, 22.7) | 6.6 (−14.7, 27.9) |
| Major abscess | 92.3 (24/26) | 90.0 (27/30) | 87.5 (2124) | −2.3 (−14.8, 10.1) | −4.8 (−18.9, 9.2) |
| Cellulitis | 58.3 (14/24) | 87.5 (21/24) | 72.7 (16/22) | 29.2 (9.2, 49.1)[c] | 14.4 (−8.4, 37.2) |
| Modified intent-to-treat | | | | | |
| Cure | 68.8 (44/64) | 80.3 (49/61) | 80.6 (50/62) | 10.1 (−2.7, 20.9) | 11.1 (−1.5, 21.7) |
| Microbiologically evaluable | | | | | |
| Cure | 69.1 (38/55) | 79.3 (46/58) | 81.3 (39/48) | 8.5 (−5.2, 20.0) | 11.0 (−2.9, 22.6) |

Note:
Cure includes cure and improvement outcomes
[a]Two patients in the intent-to-treat population were unblinded prior to completing the study. These two patients are therefore not included in any efficacy analyses (ITT N = 98), but will be included in all safety analyses (ITT, N = 100)
[b]Difference in response rate between patients by using Mantel-Haenszel method stratified by disease
[c]After data analysis was complete it was discovered that one patient randomized to the single dose group actually received 6 days of 200 mg/day. A sensitivity analysis was performed by switching the patient from single dose group to daily dose group and the statistical significance remained unchanged in the cellulitis disease category.

Figure 2:
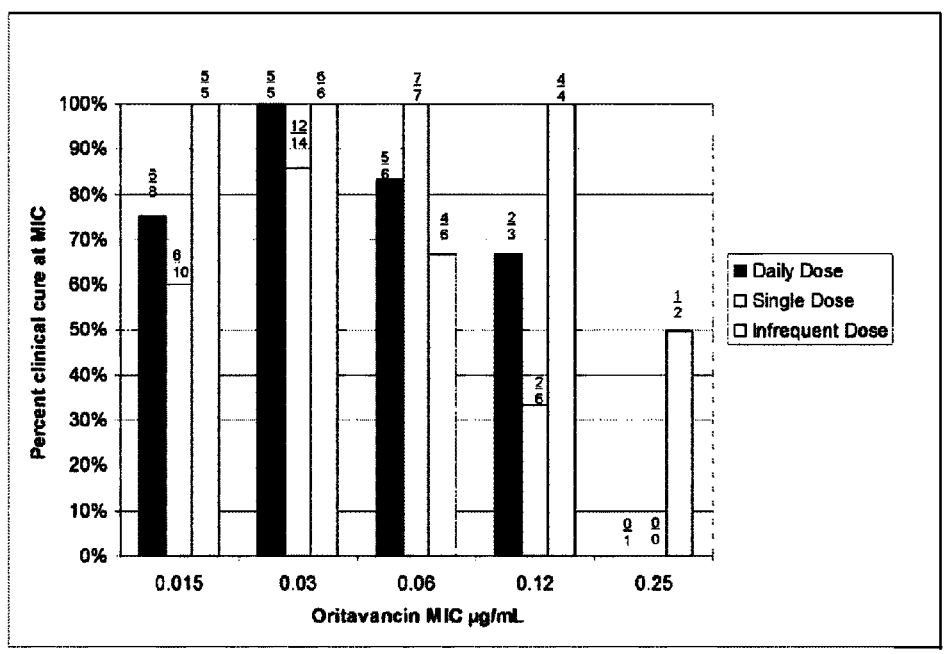
FIG. 2. Clinical cure rates for methicillin resistant *Staphylococcus aureus* by oritavancin MIC in the microbiologically evaluable population at test-of-cure.

The cure rates at TOC were 67.4%, 78.9%, and 79.5% for patients with *S. aureus* at baseline and 78.3%, 73.0%, and 87.0% for patients with MRSA at baseline in the daily dose, single dose, and infrequent dose groups, respectively (Table 4). There was no obvious relationship between oritavancin MIC and rate of cure for patients including those with *S. aureus* and MRSA at baseline at TOC in the ME population and very few isolates had a MIC above 0.12 (FIGS. 1 and 2).

TABLE 4

| Pathogen | Oritavancin 200 mg | Oritavancin 1200 mg | Oritavancin 800 mg |
|---|---|---|---|
| | % of patients cured (n of patients/total) | | |
| *Staphylococcus aureus* | 67.4 (31/46) | 78.9 (45/57) | 79.5 (31/39) |
| MRSA | 78.3 (18/23) | 73.0 (27/37) | 87.0 (20/23) |
| MSSA | 56.5 (13/23) | 90.9 (20/22) | 68.8 (11/16) |
| *Streptococcus pyogenes* | 66.7 (4/6) | 100 (1/1) | 100 (2/2) |
| *Streptococcus agalactiae* | 33.3 (1/3) | 100 (1/1) | 100 (1/1) |
| *Enterococcus faecalis* | 50.0 (2/4) | 100 (1/1) | 100 (3/3) |

Note:
Cure includes cure and improvement outcomes

Relapse rates in CE patients were low with no patients in the daily dose group, 1/61 (1.6%) patients in the single, and 2/54 (3.7%) patients in the infrequent dose groups experiencing relapse. In the ITT population the mean duration of study medication (oritavancin or placebo) was similar in the daily, single, and infrequent dose groups, (5.4, 5.1, and 5.2 days, respectively).

Safety and Tolerability. Overall, safety findings were comparable between the three treatment groups. The most common reason for early discontinuation of study medication was lack of efficacy (3.3%, 10/302). The most common adverse events were nausea, phlebitis, diarrhea, headache, infusion site extravasation, vomiting, and constipation. There was a higher incidence of blood creatine phosphokinase (CPK) increase in the single dose group compared to the daily and infrequent dose groups. Review of these cases showed that patients with increases in CPK had mild, asymptomatic elevations from normal or were already slightly elevated at baseline. Most had normalized by last visit. In one subject the elevation was only observed at day 35.

The majority of adverse events were considered by the investigator to be mild or moderate in intensity (85.7%, 94.5%, and 95.2% in the daily, single, and infrequent dose groups, respectively) with more than half in each treatment group being mild (51.8%, 58.2%, and 60.3%). The majority of adverse events were unrelated to study medication. Of the adverse events that the investigator recorded as related to study medication, phlebitis, diarrhea, and nausea were the most common. The percentage of patients with phlebitis that was assessed by the investigator as being related to study medication was 3.0% (3/100), 4.0% (4/99), and 8.7% (9/103) in the daily, single, and infrequent dose groups, respectively and none of the phlebitis events were severe. In the infrequent dose group the percentage of patients with related phlebitis was 11.8% (4/34) in patients who received 800 mg only and 7.2% (5/69) in patients who received 800 mg plus the 400 mg dose.

A total of 25 patients (8.3%) had a serious adverse event. The incidence of serious adverse events was higher in the daily dose group (11%, 11/100) compared to the single dose group (7.1%, 7/99), and the infrequent dose group (6.8%, 7/103). Two patients in the single dose group had a serious adverse event that was investigator-assessed as being related to study medication. One patient suffered dyspnoea and the other patient suffered hypersensitivity. Five patients died during the study (3/100 in the daily dose group, 0/99 in the single dose group, and 2/103 in the infrequent dose group). The adverse events leading to the deaths were cardiac arrest, cardiopulmonary failure, septic shock, myocardial infarction, and pulmonary embolism. None of the deaths were investigator-assessed as being related to study medication and no patients died during therapy. A total of seven patients discontinued study medication due to an adverse event (3.0%

[3/100], 3.0% [3/99], and 1.0% [1/103] in the daily, single, and infrequent dose groups, respectively). The adverse events leading to early discontinuation of study medication were abscess, gangrene, catheter site pain, renal impairment, eye pruritis, and hypersensitivity (2 patients).

Vital signs data were unremarkable and typical of patients being treated for complicated skin and skin structure infections. There were no clinically significant treatment group differences in these parameters or any indication of unexpected adverse systemic effects of the treatment.

The evidence provided by this study demonstrates that oritavancin given as a single dose of 1200 mg or an infrequent dose of 800 mg with an optional 400 mg on Day 5 is non-inferior to a 200 mg daily dose for 3 to 7 days in treatment of patients with complicated skin and skin structure infections. This study provides evidence for the effectiveness of single dose or infrequent dosing of oritavancin in the treatment of cSSSI. Single and infrequent doses of oritavancin were as efficacious as daily doses for complicated skin and skin structure infections caused by gram-positive pathogens, including MRSA. Safety and tolerability were similar among dosing groups.

Example 2

Comparative Efficacy of Oritavancin (ORI) Against Methicillin-Sensitive and -Resistant *Staphylococcus aureus* Strains in a Neutropenic-Mouse Thigh Infection Model Oritavancin (ORI) is a novel lipoglycopeptide with a highly potent in vitro activity against most gram-positive bacteria including penicillin-resistant *Streptococcus pneumoniae*, methicillin-resistant *Staphylococcus aureus* (MRSA) and vancomycin (VAN)-resistant *Enterococci* (VRE) (Allen, N. E. and T. I. Nicas, FEMS Microbiol Rev 26(5): 511-32 (2003); Arhin et al., Antimicrob Agents Chemother 52(5): 1597-603 (2008)).

In this study, single bolus and human equivalent (HEQ) doses of Oritavancin (ORI) were used to compare its activity against MSSA and MRSA clinical isolates in a murine thigh-infection model.

Methods: Thigh infection was established for 14 clinical SA isolates (3 MSSA and 11 MRSA; MICs 0.0015 to 2 μg/mL) in neutropenic CD-1 mice (n=3/group) with 5×10$^5$ colony forming units (CFU) of cells. Single intravenous doses of ORI (0.5 to 40 mg/kg) were tested against one MSSA and one MRSA strain. Efficacy of ORI doses simulating human exposure (HEQ doses, i.e. 24 h AUC-matched) of 100 or 200 or 400 mg daily×3 days, and a single 1200 mg HEQ dose were also evaluated against the MSSA and MRSA strains. Both thighs were harvested and CFU counts were evaluated after 24 h (single doses) or 72 h (HEQ doses) treatment.

Strains: Fourteen clinical *S. aureus* isolates (3 MSSA and 11 MRSA; MICs 0.0015 to 2 μg/mL) were used in this study. MICs were determined by the broth microdilution assay against oritavancin following CLSI guidelines and included polysorbate-80 (final test concentration of 0.002%) as described previously (Arhin et al., Antimicrob Agents Chemother 52(5): 1597-603 (2008)).

In vivo studies: All studies were performed in accordance with protocols that were approved by the Institutional Animal Care and Use Committee. Thigh infection was established for 14 clinical *S. aureus* isolates in neutropenic CD-1 mice (19-21 g, n=3/group) with 5×10$^5$ colony forming units (CFU) of cells in both thighs. In the single dose-response study, the number of bacteria/thigh was monitored 24 h post-infection (PI). In the human equivalent (HEQ) dose-ranging study, the bacterial titer was determined in mouse thighs at 2, 4, 8, 12, 24, 48 and 72 h PI. Thighs were serially diluted and plated on Baird-Parker agar plates to determine the bacterial titer. The limit of detection was 1.69 Log$_{10}$ CFU/thigh. Bacterial titer decreases were calculated (compared to starting inoculum) in thighs at 72 h PI for each HEQ dose regimen of ORI.

Antibiotherapy: 1) In the single dose response study, mice were treated intravenously (IV) with ORI at doses ranging from 0.4 to 40 mg/kg at 1h PI. 2) In the HEQ dose-ranging study, starting at 1 h PI, the mice received a multiple IV dose regimen to simulate human drug concentration profile. The following HEQ doses were simulated: daily doses (QD) of 100, 400, 800 mg for 72 h, or a single 1200 mg dose (Lehoux et al. "Efficacy of Oritavancin (ORI) in the Mouse Bacteremia Model." 48th Interscience Conference on Antimicrobial Agents and Chemotherapy; 2008 September 25-28; Washington (DC) Poster B-1009).

Data analysis: The inhibitiory sigmoid $E_{max}$ model was used to calculate the ED$_{50}$ of oritavancin (dose resulting in 50% of the maximal bacterial killing) ±95% confidence interval by using the GraphPad Prism software. The statistical calculations to compare bacterial titer from each experimental group were performed according to the Mann-Whitney U test by using StatsDirect software. p-values below 0.05 were considered significant.

Figure 3:
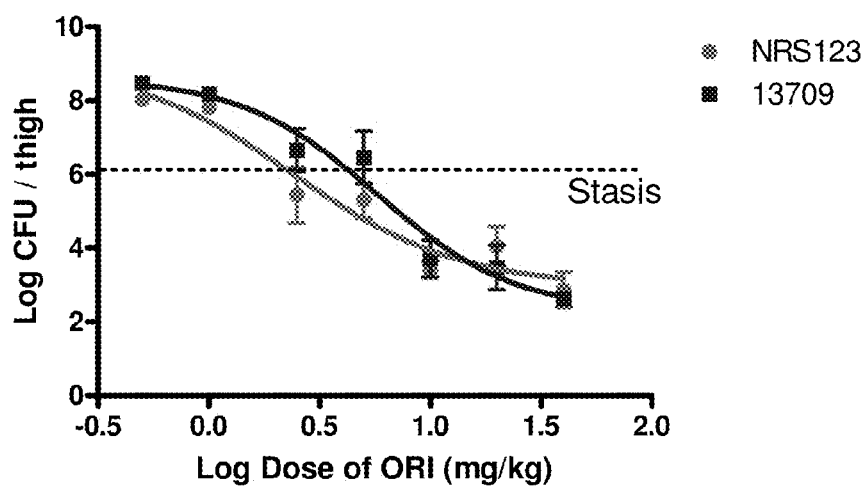
FIG. 3. Comparative single dose-response study of oritavancin against MSSA and MRSA in the neutropenic-mouse thigh infection model. Infection caused by *S. aureus* ATCC13709 (MSSA) and NRS123 (MRSA). Similar $ED_{50}$: 5.8 (3.3-10) and 2.4 (0.8-7.3) mg/kg for ATCC13709 and NRS123, respectively.
Figure 4:
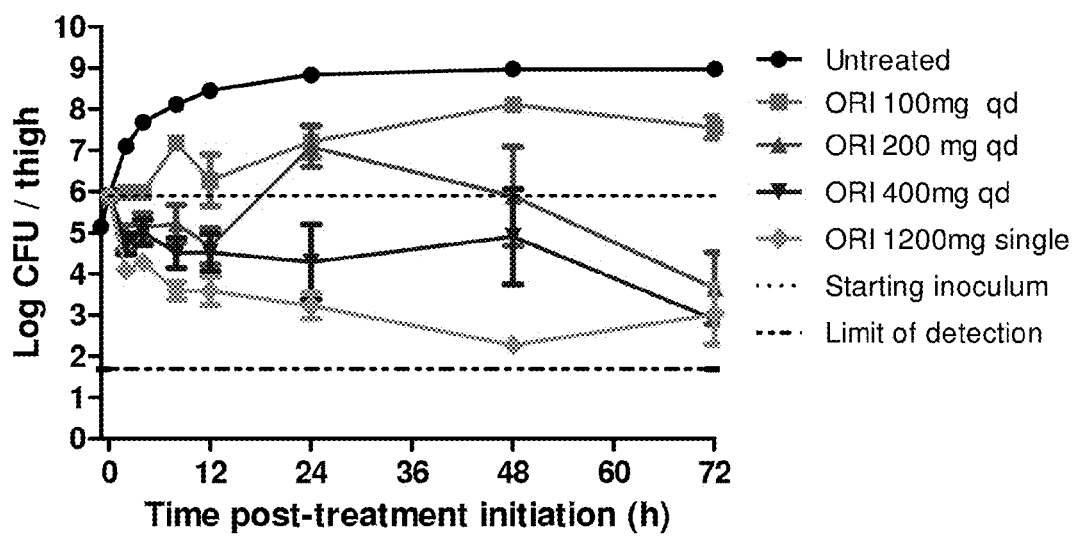
FIG. 4. Efficacy of HEQ dose of oritavancin in the neutropenic-mouse thigh infection model (mean±SEM). Infection caused by *S. aureus* ATCC13709. A dose-response relationship is observed with >2-Log kill for 200, 400 and 1200 mg at 72 h.
Figure 5:
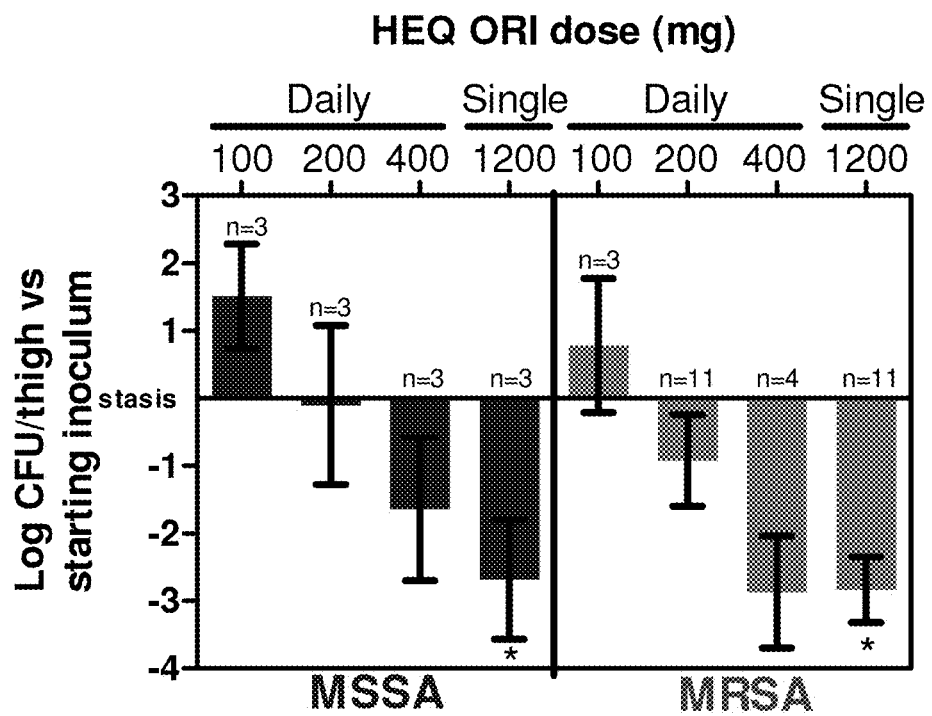
FIG. 5. Efficacy of oritavancin against MSSA or MRSA strains in the neutropenic-mouse thigh infection model at 72 h post-infection (mean with 95% CI). * p-value <0.05 compared to the 200 mg HEQ dose. In vivo efficacy is not affected by the oxacillin resistance phenotype. Oritavancin was active against all tested strains, independently of their MIC.

Results: The single dose dose-response studies of ORI yielded similar ED$_{50}$ (dose resulting in 50% of the maximal killing): 5.8 mg/kg (95% CI: 3.3-10) for MSSA and 2.4 mg/kg (95% CI: 0.8-7.3) for MRSA (FIG. 3). Also, efficacy of ORI was HEQ dose-dependent (FIG. 4). ORI was similarly efficacious against MSSA and MRSA strains (FIG. 5). Bacterial load reduction was significantly higher for the single 1200 mg dose compared to the 200 mg daily dose (p<0.0005) (Table 5).

TABLE 5

| | Mean Log CFU/thigh from baseline | | | |
|---|---|---|---|---|
| | MSSA | | MRSA | |
| HEQ Dose | mean | 95% CI | mean | 95% CI |
| 100 mg × 3 days | 1.5 (n = 3) | 0.7 to 2.3 | 0.8 (n = 3) | −0.2 to 1.8 |
| 200 mg × 3 days | −0.1 (n = 3) | −1.3 to 1.1 | −0.9 (n = 11) | −1.9 to −0.2 |
| 400 mg × 3 days | −1.6 (n = 3) | −2.7 to −0.6 | −2.8 (n = 3) | −3.7 to −2.0 |
| 1200 mg × 1 day | −2.7 (n = 3) | −3.6 to −1.8 | −2.8 (n = 11) | −3.3 to −2.3 | n = number of strains tested

Conclusions: ORI was equivalently efficacious against MSSA and MRSA in vivo. The single dose-response study (1200 mg) revealed that ORI is equivalently efficacious (similar EDO against MSSA and MRSA in the thigh model.

Example 3

A pharmacokinetic (PK) analysis was conducted of oritavancin from patients having complicated skin and skin structure infections (cSSSI) or bacteremia. The population for the analysis consisted of oritavancin-treated subjects and patients from 12 studies, consisting of nine Phase 1 studies, two Phase 2 studies, and one Phase 2/3 study. Oritavancin was administered as both single- and multiple-dose intravenous (IV) infusions in fixed doses ranging from 100 to 800 mg or weight-based doses ranging from 0.02 to 10 mg/kg.

Results: The final analysis population contained data from a total of 560 subjects: 200 from the Phase 1 studies, 86 from the Phase 2 bacteremia study, 29 from the Phase 2 cSSSI study, and 245 from the Phase 2/3 cSSSI study. The final pharmacokinetic analysis dataset contained a total of 6,336 oritavancin plasma concentrations, collected from these 560 subjects, of which 6,290 oritavancin concentrations were included in the results. The majority of subjects (>90%) contributed at least six samples to the population pharmacokinetic analysis.

Figure 6:
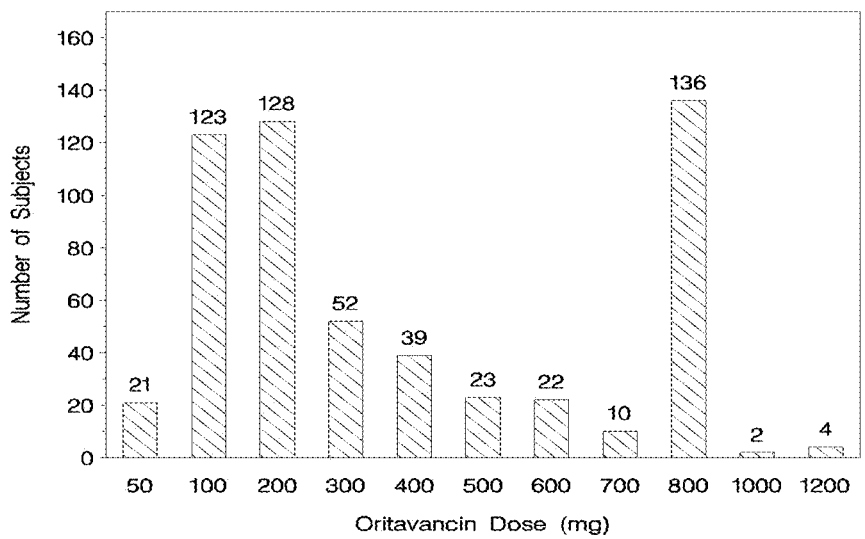
FIG. 6. Histogram of oritavancin doses administered.
Figure 7:
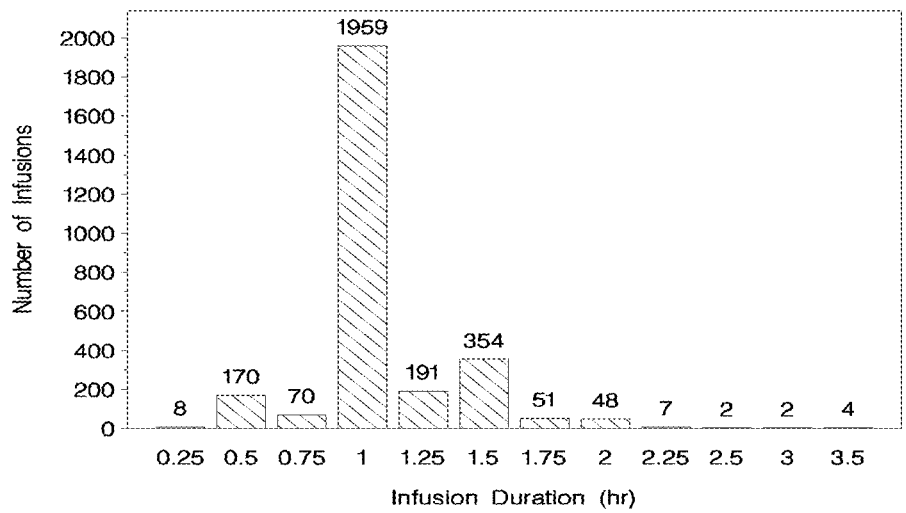
FIG. 7. Histogram of oritavancin infusion durations.
Figure 8:
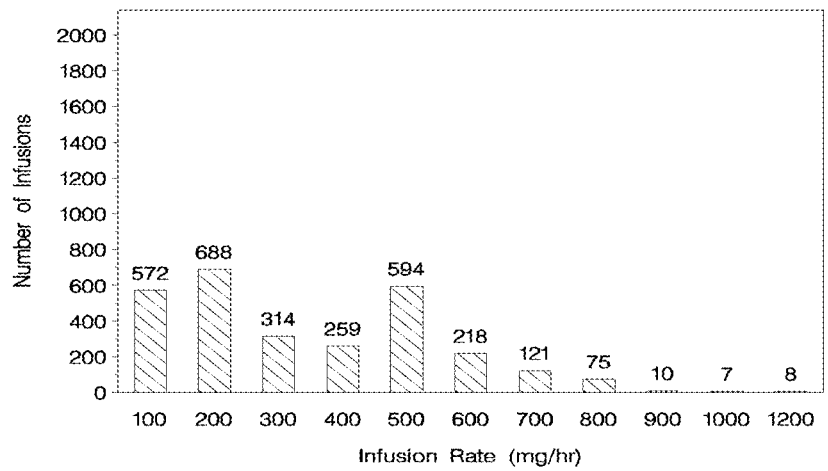
FIG. 8. Histogram of oritavancin infusion rates.

A wide range of oritavancin doses was administered across the studies included in the population PK analysis, where 42% (236 of 560) of subjects received ≧400 mg, while 25% (142 of 560) received 800 mg or more. A histogram of the oritavancin doses administered is shown in FIG. 6, with midpoint values for each dose range shown over each bar. The duration over which oritavancin was infused ranged from 0.13 to 6.5 hr across all studies; however, oritavancin was administered over 1 hr for the majority of subjects. Histograms of the actual infusion durations and rates are shown in FIGS. 7 and 8, respectively, with midpoint values shown for each infusion duration or rate over each bar.

The range of doses allowed for a robust assessment of the dose-proportionality (also termed linearity) of the PK of oritavancin. Although a formal statistical assessment of dose-proportionality was not performed, the goodness-of-fit of the final population PK model was used to detect any apparent lack of dose-proportionality.

The final structural PK model for oritavancin in this analysis was a three-compartment model (one central, two peripheral) with a zero-order intravenous infusion rate and first-order, linear elimination. The model fit the data well (data not shown), regardless of the observed concentration or administered dose. If a nonlinear model had been necessary, there would have been significant bias in the weighted residuals at the lowest and/or highest concentrations and/or doses. No trends for decreasing CL with increasing dose were found. The summary statistics of key PK parameter estimates, stratified by dose, are provided in Table 6.

TABLE 6

| Variable | <180 mg/day (n = 181) | | 180-330 mg/day (n = 140) | | >330 mg/day (n = 239) | |
|---|---|---|---|---|---|---|
|  | Mean (SD) | Median (Min-Max) | Mean (SD) | Median (Min-Max) | Mean (SD) | Median (Min-Max) |
| Dose (mg) | 114 (37.9) | 113 (1.00-179) | 239 (40.4) | 231 (180-330) | 682 (179) | 800 (333-1220) |
| CL (L/hr) | 0.558 (0.194) | 0.550 (0.169-1.40) | 0.574 (0.219) | 0.544 (0.208-1.45) | 0.441 (0.202) | 0.401 (0.121-1.43) |
| $T_{1/2,\alpha}$ (hr) | 2.01 (0.467) | 1.97 (0.939-3.55) | 2.13 (0.460) | 2.13 (0.910-3.27) | 2.45 (0.643) | 2.35 (1.03-4.78) |
| $T_{1/2,\beta}$ (hr) | 27.4 (7.89) | 27.5 (8.37-58.3) | 29.7 (9.97) | 29.3 (10.4-81.5) | 31.4 (14.2) | 29.3 (9.38-99.6) |
| $T_{1/2,\gamma}$ (hr) | 376 (71.1) | 387 (142-567) | 376 (77.5) | 373 (192-545) | 353 (80.8) | 347 (166-302) |
| $AUC_{0-24}$ (µg * h/mL) | 90.0 (61.7) | 73.6 (1.02-519) | 181 (77.1) | 171 (46.5-424) | 750 (412) | 712 (109-2090) |
| Cmax (µg/mL) | 17.8 (11.5) | 14.3 (0.156-87.2) | 33.4 (13.2) | 30.0 (12.4-92.7) | 106 (42.2) | 105 (20.4-251) |
| Cmin (µg/mL) | 1.17 (0.813) | 0.949 (0.016-6.78) | 2.58 (1.45) | 2.20 (0.452-8.00) | 12.5 (8.74) | 11.0 (1.41-40.7) |

Figure 9:
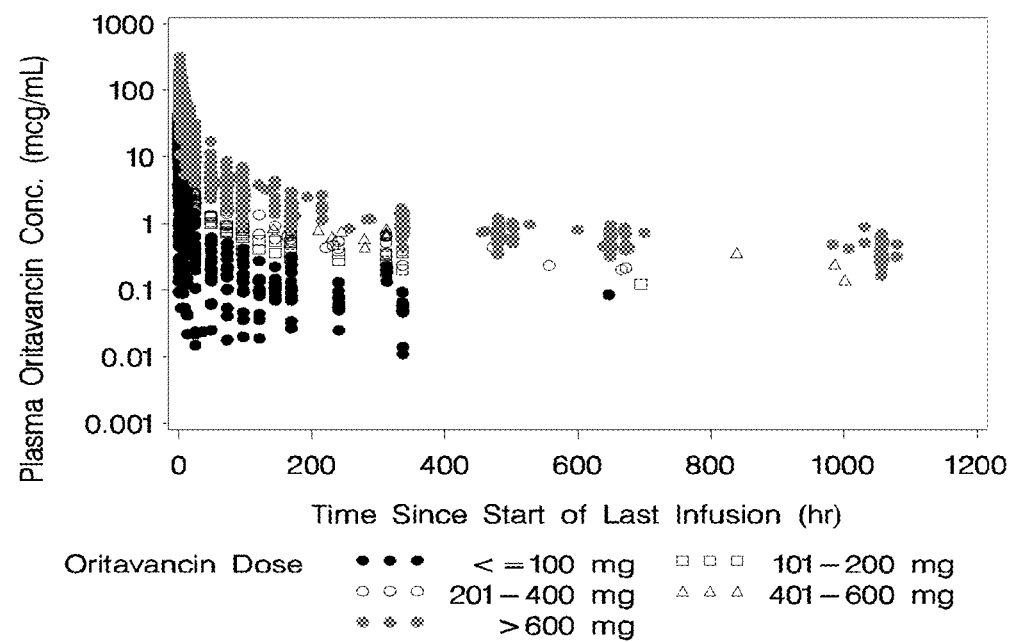
FIG. 9. Semilog scatterplot of oritavancin concentrations versus time since start of last infusion, stratified by dose range, following a single dose of oritavancin.

A semilog scatterplot of oritavancin concentrations versus time since start of last infusion, stratified by dose range, following a single dose of oritavancin is shown in FIG. 9. The summary statistics of key PK parameter estimates for healthy subjects are provided in Table 7.

TABLE 7

| Variable | Single Dose (n = 91) | Multiple Dose (n = 109) |
|---|---|---|
| CL (L/hr) | 0.402 (26.0) | 0.309 (30.2) |
| Vc (L) | 5.30 (20.0) | 5.10 (28.1) |
| $T_{1/2,\alpha}$ (hr) | 2.25 (24.4) | 2.82 (22.0) |
| $T_{1/2,\beta}$ (hr) | 19.8 (28.2) | 33.0 (35.3) |
| $T_{1/2,\gamma}$ (hr) | 316 (16.9) | 320 (19.9) |
| $AUC_{0-24}$ (mg · hr/L)[a] | 216 (28.6) | 459 (160)[b] |
| Cmax (µg/mL)[a] | 33.9 (22.5) | 46.8 (14.0)[b] |
| Cmin (µg/mL)[a] | 3.30 (41.8) | 11.5 (4.71)[b] |

[a]$AUC_{0-24}$, Cmax, and Cmin have been normalized to a dose of 200 mg to ease comparisons across groups.
[b]Exposure parameters obtained after a median (min-max) of 4 (2-14) days.

It is understood that the examples and embodiments described herein are for illustrative purposes only and that various modifications or changes in light thereof will be suggested to persons skilled in the art and are to be included within the spirit and purview of this application and scope of the appended claims.

All documents, including but not limited to publications, patents, patent applications, books, manuals, articles, papers, abstracts, and posters, and other materials referenced herein are expressly incorporated herein by reference in their entireties.

We claim:

1. A method of treating a complicated skin and skin structure infection (cSSSI) in a subject, comprising administering a single dose of a therapeutically effective amount of a pharmaceutical composition comprising oritavancin, or a pharmaceutically acceptable salt thereof, and a pharmaceutically acceptable carrier or diluent, over a course of therapy to a subject having cSSSI, wherein the single dose comprises at least 1200 mg oritavancin, or a pharmaceutically acceptable salt thereof, thereby treating cSSSI in the subject.

2. The method of claim 1, wherein the single dose comprises between 1200 mg to 1800 mg oritavancin, or a pharmaceutically acceptable salt thereof.

3. The method of claim 1, wherein said administering is via intravenous administration or oral administration.

4. The method of claim 1, wherein the bacteria causing cSSSI a is one or more bacteria selected from the group consisting of a gram-positive bacteria, *Staphylococcus aureus*, methicillin-resistant *Staphylococcus aureus*, vancomycin-resistant *Staphylococcus aureus*, vancomycin-intermediate *Staphylococcus aureus*, vancomycin hetero-intermediate *Staphylococcus aureus, Streptococcus pyogenes, Streptococcus agalactiae, Streptococcus anginosus, Streptococcus intermedius, Streptococcus constellatus, Streptococcus dysgalactiae, Streptococcus dysgalactiae* subsp. *equisimilis, Enterococcus faecalis*, vancomycin-resistant *Enterococcus faecalis, Enterococcus faecium*, and vancomycin-resistant *Enterococcus faecium*.

* * * * *